US008367412B2

(12) United States Patent
Yamaguchi et al.

(10) Patent No.: US 8,367,412 B2
(45) Date of Patent: Feb. 5, 2013

(54) PROTEIN CRYSTALLIZING AGENT AND METHOD OF CRYSTALLIZING PROTEIN THEREWITH

(75) Inventors: Hiroshi Yamaguchi, Sanda (JP); Len Ito, Sanda (JP)

(73) Assignee: Kwansei Gakuin Educational Foundation, Hyogo (JP)

( * ) Notice: Subject to any disclaimer, the term of this patent is extended or adjusted under 35 U.S.C. 154(b) by 0 days.

(21) Appl. No.: 12/449,657

(22) PCT Filed: Sep. 19, 2007

(86) PCT No.: PCT/JP2007/068192
§ 371 (c)(1),
(2), (4) Date: Aug. 20, 2009

(87) PCT Pub. No.: WO2008/102469
PCT Pub. Date: Aug. 28, 2008

(65) Prior Publication Data
US 2010/0095749 A1    Apr. 22, 2010

(30) Foreign Application Priority Data
Feb. 23, 2007 (JP) .................................. 2007-044275

(51) Int. Cl.
*G01N 31/02* (2006.01)
*G01N 33/483* (2006.01)
(52) U.S. Cl. .................. 436/4; 436/86; 436/87; 436/181
(58) Field of Classification Search .......... 436/4, 86–87, 436/181; 422/245.1
See application file for complete search history.

(56) References Cited

U.S. PATENT DOCUMENTS

| | | | | |
|---|---|---|---|---|
| 4,568,544 A | * | 2/1986 | Hasegawa et al. | 424/94.1 |
| 4,678,566 A | * | 7/1987 | Watanabe et al. | 210/143 |
| 4,795,806 A | * | 1/1989 | Brown et al. | 530/383 |
| 5,064,767 A | * | 11/1991 | Le et al. | 436/89 |
| 5,096,676 A | * | 3/1992 | McPherson et al. | 117/206 |
| 5,130,105 A | * | 7/1992 | Carter et al. | 422/215 |
| 5,260,420 A | * | 11/1993 | Burnouf-Radosevich et al. | 530/382 |
| 5,262,312 A | * | 11/1993 | Holla et al. | 435/101 |

(Continued)

FOREIGN PATENT DOCUMENTS
JP   2000-510161   8/2000
JP   2006-512416   4/2006

(Continued)

OTHER PUBLICATIONS
Aldrich Catalog, 1988, p. 1611.*

(Continued)

*Primary Examiner* — Arlen Soderquist
(74) *Attorney, Agent, or Firm* — Wenderoth, Lind & Ponack, L.L.P.

(57) ABSTRACT

The present invention provides a technique for crystallizing a desired protein at a high probability; namely, a protein crystallizing agent and a method of crystallizing protein. The present invention also provides a technique for determining the conditions for protein crystallization easily with high efficiency; namely, a method of screening the conditions for protein crystallization and a protein crystallization screening reagent. As the protein crystallizing agent, at least one compound selected from the group consisting of a basic amino acid, acidic amino acid, ester derivative of amino acid and amide derivative of amino acid is used, or at least one of these compounds is used in combination with another protein crystallizing agent.

10 Claims, 8 Drawing Sheets

U.S. PATENT DOCUMENTS

| | | | | |
|---|---|---|---|---|
| 5,318,782 | A * | 6/1994 | Weis-Fogh | 424/529 |
| 5,405,767 | A * | 4/1995 | Shetty et al. | 435/195 |
| 5,419,278 | A * | 5/1995 | Carter | 117/206 |
| 5,446,024 | A * | 8/1995 | Builder et al. | 514/8.5 |
| 5,552,318 | A * | 9/1996 | Houng et al. | 435/280 |
| 5,622,846 | A * | 4/1997 | Kiener et al. | 435/128 |
| 5,641,681 | A * | 6/1997 | Carter | 436/4 |
| 5,932,551 | A * | 8/1999 | Caldwell et al. | 514/19 |
| 5,997,636 | A * | 12/1999 | Gamarnik et al. | 117/70 |
| 6,267,935 | B1 * | 7/2001 | Hol et al. | 422/245.1 |
| 6,268,158 | B1 * | 7/2001 | Pantoliano et al. | 435/7.1 |
| 6,387,890 | B1 * | 5/2002 | Christianson et al. | 514/64 |
| 6,479,671 | B1 * | 11/2002 | Konoike et al. | 549/23 |
| 6,541,606 | B2 * | 4/2003 | Margolin et al. | 530/350 |
| 6,602,714 | B1 * | 8/2003 | Tagge et al. | 506/37 |
| 6,645,490 | B2 * | 11/2003 | Yarkoni et al. | 424/134.1 |
| 6,916,455 | B2 * | 7/2005 | Segelke et al. | 422/245.1 |
| 7,015,041 | B2 * | 3/2006 | Santarsiero et al. | 436/4 |
| 7,074,896 | B1 * | 7/2006 | Sondermann et al. | 530/350 |
| 7,214,540 | B2 * | 5/2007 | DeLucas et al. | 436/86 |
| 7,247,203 | B2 | 7/2007 | Sasaki et al. | |
| 7,550,567 | B2 * | 6/2009 | Metzner et al. | 530/382 |
| 2002/0090374 | A1 * | 7/2002 | Yarkoni et al. | 424/178.1 |
| 2003/0008807 | A1 * | 1/2003 | Levine et al. | 514/1 |
| 2003/0120042 | A1 * | 6/2003 | Yamada et al. | 530/350 |
| 2003/0180960 | A1 * | 9/2003 | Cosenza et al. | 436/86 |
| 2005/0062196 | A1 * | 3/2005 | Hansen et al. | 264/219 |
| 2005/0226893 | A1 * | 10/2005 | Juneau et al. | 424/204.1 |
| 2005/0241568 | A1 | 11/2005 | Sasaki et al. | |
| 2006/0093613 | A1 * | 5/2006 | Jakobsen et al. | 424/185.1 |
| 2006/0093678 | A1 * | 5/2006 | Chickering et al. | 424/489 |
| 2007/0178166 | A1 * | 8/2007 | Bernstein et al. | 424/499 |
| 2007/0249988 | A1 * | 10/2007 | Padmanabhan et al. | 604/20 |
| 2009/0176692 | A1 * | 7/2009 | Habermann et al. | 514/4 |

FOREIGN PATENT DOCUMENTS

| | | |
|---|---|---|
| WO | 98/34953 | 8/1998 |
| WO | 2004/018744 | 3/2004 |
| WO | 2004-060310 | 7/2004 |

OTHER PUBLICATIONS

Vasco-Mendez, N. L. et al, Journal of Agriculture and Food Chemistry 1999, 47, 862-866.*
Beretta, S. et al, Macromolecules 2000, 33, 8663-8670.*
Tamagawa, R. E. et al, Crystal Growth & Design 2002, 2, 511-514.*
McPherson, A., Methods 2004, 34, 254-265.*
Johnson, A. R. et al, Protein Science 1996, 5, 382-390.*
Gao, J. et al, Journal of Pharmaceutical Sciences 1998, 87, 246-248.*
Poinsot, V. et al, Electrophoresis 2006, 27, 176-194.*
ADDit TM Additive Screen, [online]. B-Bridge Newsletter, 2005, p. 28, retrieved from the Internet (English abstract).
ADDit TM Additive Screen, technical sheet [online]. B-Bridge International, Inc. 2004, retrieved from the Internet (English abstract).
H. Adachi et al., "Effect of Short Pulse Laser on Organic and Protein Crystal Growth", The Japanese Association for Crystal Growth, vol. 29, No. 5, 2002 (with English abstract). pp. 35-39.
H. Adachi et al., "Growth of High-quality and Large Protein Crystals at Interface between Two Liquids Using Slow Cooling Method", The Japanese Association for Crystal Growth, vol. 29, No. 3, 2002 (with English abstract), pp. 55-59.
K. Shiraki et al., "Amino Acid Esters Prevent Thermal Inactivation and Aggregation of Lysozyme", Biotechnol. Prog., vol. 21, pp. 640-643, 2005.
Thoden, James B., et al., "Crystallization and preliminary X-ray Crystallographic analysis of carbamoyl phosphate synthetase from *Escherichia coli*", Acta Cryst., 1995, D51, pp. 827-829.

* cited by examiner

< Condition of Crystallization >
hanging-drop vapor-diffusion method
- Buffer :        0.1 M Na Phosphate (pH 6.5)
- Precipitant :   17.5 % PEG 3350
- Protein :       4.1 % Hemoglobin
- Temperature :   20 °C No additive Asp GlyEE

US 8,367,412 B2

PROTEIN CRYSTALLIZING AGENT AND METHOD OF CRYSTALLIZING PROTEIN THEREWITH

This application is a US National Stage of International Application No. PCT/JP2007/068192 filed Sep. 19, 2007.

TECHNICAL FIELD

The present invention relates to a protein crystallization accelerator and a protein crystallizing agent, which can be used to obtain protein crystals from a protein-containing solution by accelerating precipitation of protein crystals. The present invention further relates to a method for precipitating protein crystals from a protein-containing solution. The present invention also relates to a method for screening conditions of protein crystallization from a protein-containing solution, and to a reagent for use therefor.

BACKGROUND ART

In present post-genome research, attempts have been made to discover drugs based on protein's three-dimensional structure; therefore, there is an urgent need for protein structure analysis. An optimal technique for protein structure analysis is crystal structure analysis. However, protein crystallization, an essential step of crystal structure analysis, is currently very difficult because the success rate is low, a considerable amount of time is required, etc. For this reason, protein crystallization is a hindrance in the three-dimensional structure analysis of proteins, and for drug discoveries utilizing them.

Generally, in order to precipitate a protein crystal from a protein-containing solution, the degree of supersaturation must be made high by means of either a solvent vaporization, a temperature change, or a precipitant. When the degree of supersaturation is low, nucleation may not occur, nucleation and crystal growth may be delayed, etc. Conversely, when the degree of supersaturation is too high, crystals are abruptly precipitated and undergo rapid growth, causing quality defects in the obtained crystals; further, an amorphous precipitate separated from the solution is likely to be produced. Usually, the crystallization conditions are determined as a result of trial and error by actually making several to a great number of attempts at crystallization; however, this requires a great deal of labor and time, and is thus inefficient.

In order to solve the above problems, a method for producing crystals within a short period of time by irradiating a protein-containing solution with a short-pulse laser so as to force the nuclei of crystals to generate, then stirring the solution, has been developed (see Non-Patent Document 1, Patent Document 1, etc.). Additionally, as a method suitable for growing high-quality large-sized protein crystals, a method comprising growing a crystal on the interfaces of two liquids upon decrease of the temperature has been proposed (see Non-Patent Document 2, etc.).

On the other hand, reagent kits for screening protein crystallization conditions, which utilize the crystallization-accelerating properties of certain precipitants and buffers (for example, products from Hampton Research Corp., Emerald BioStructures, Inc., Jena Bioscience GmbH, Molecular Dimensions Ltd., etc.), are commercially available. There is no clear theory about protein crystallization. A technique generally utilized therefor is to first find crystallization conditions by carrying out a screening under a wide range of conditions (an initial screening or a random screening), and subsequently narrowing the obtained crystallization conditions down to the optimal crystallization conditions (the elaboration of conditions). Therefore, according to the above process, it can be said that success of crystallization of a target protein relies on whether crystallization conditions can be found during the initial screening. Further, in order to crystallize a target protein, the target protein must have high purity suitable for crystallization.

The above-mentioned commercially available reagent kits for screening crystallization conditions are useful because it can be easily utilized. However, the reagent kits do not always obtain crystals in high probability; therefore, the development of a screening reagent that can precipitate protein crystals in higher probability is anticipated. There is also a demand for a reagent that makes the crystallization of proteins with low purity possible.

Patent Document 1: WO 2004/018744
Non-Patent Document 1: Journal of the Japanese Association of Crystal Growth, Vol. 29, No. 5, 2002
Non-Patent Document 2: Journal of the Japanese Association of Crystal Growth, Vol. 29, No. 3, 2002

DISCLOSURE OF THE INVENTION

Problems to be Solved by the Invention

An object of the present invention, which is accomplished in view of the above circumstances, is to provide a technique for crystallizing a target protein in high probability (a protein crystallization accelerator, a protein crystallizing agent, and a method for crystallizing protein). It is a further object of the present invention to provide a technique for readily and effectively finding and determining protein crystallization conditions (a method for screening protein crystallization conditions and a protein crystallization screening reagent).

Means for Solving the Problems

The present inventor carried out intensive research to achieve the above object, and found that the addition of a small molecule such as specific amino acids, ester derivatives of amino acids, amide derivatives of amino acids, and the like to a protein-containing solution accelerates precipitation of protein crystals; and that a protein is thereby crystallized in high probability. Further, the inventor confirmed that the above small molecules function as a protein crystallization accelerator, and that the low molecule compounds can be effectively used, as a protein crystallizing agent, singly or in combination with a well-known protein crystallizing agent, such as precipitants, pH buffers, etc. Additionally, the inventor found that the addition of the above low molecule compounds to a protein-containing solution enables precipitation of crystals, even under conditions in which the precipitation of protein crystals would not occur, and even with proteins with a slightly low purity. Thereby, the inventor confirmed that the small molecules can also be effectively used as a screening reagent for evaluating protein crystallization conditions.

The present invention is completed based on the above findings, and encompasses the following aspects.

(I) Protein Crystallization Accelerator (I-1) A protein crystallization accelerator comprising, as an active ingredient, at least one compound selected from the group consisting of basic amino acids, acidic amino acids, ester derivatives of amino acids, amide derivatives of amino acids, and salts and solvates thereof.

(I-2) The protein crystallization accelerator according to (I-1), wherein the basic amino acids are arginine, lysine and ornithine; the acidic amino acids are aspartic acid and glutamic acid; the ester derivatives of amino acids are glycine ethyl ester, lysine ethyl ester, and serine ethyl ester; and the amide derivatives of amino acids are glycinamide, serinamide, threonine amide, argininamide, and prolinamide.

(II) Protein Crystallizing Agent (II-1) A protein crystallizing agent consisting of at least one compound selected from the group consisting of basic amino acids, acidic amino acids, ester derivatives of amino acids, amide derivatives of amino acids, and salts and solvates thereof; or a protein crystallizing agent comprising at least one compound selected from the above group.

(II-2) The protein crystallizing agent according to (II-1), wherein the basic amino acids are arginine, lysine and ornithine; the acidic amino acids are aspartic acid and glutamic acid; the ester derivatives of amino acids are glycine ethyl ester, lysine ethyl ester, and serine ethyl ester; and the amide derivatives of amino acids are glycinamide, serinamide, threonine amide, argininamide, and prolinamide.

(II-3) The protein crystallizing agent according to (II-1), which comprises at least one compound selected from the group consisting of arginine, lysine, ornithine, glycine ethyl ester, serine ethyl ester, lysine ethyl ester, glycinamide, serinamide, threonine amide, argininamide, and prolinamide.

(II-4) The protein crystallizing agent according to (II-1) or (II-2), which essentially consists of a combination of at least one compound selected from the group consisting of basic amino acids, acidic amino acids, ester derivatives of amino acids, amide derivatives of amino acids, and salts and solvates thereof; and at least one component selected from the group consisting of precipitants and pH buffers.

(III) Method for Crystallizing Protein (III-1) A method for crystallizing protein, comprising the steps of:

bringing the protein crystallization accelerator of (I-1) or (I-2), or the protein crystallizing agent of any one of (II-1) to (II-4) into contact with a protein-containing solution; and precipitating the protein.

(III-2) The method for crystallizing protein according to (III-1), comprising the steps of:

using, in a vapor diffusion method, a batch method, a liquid-liquid diffusion method or a dialysis method, the protein crystallization accelerator of (I-1) or (I-2) as a protein crystallization accelerator, or the protein crystallizing agent of any one of (II-1) to (II-4) as a protein crystallizing agent;

bringing the protein crystallization accelerator or the protein crystallizing agent into contact with the protein-containing solution; and precipitating the protein.

(IV) Method for Screening Protein Crystallization Conditions (IV-1) A method for screening protein crystallization conditions, comprising the steps of:

bringing the protein crystallization accelerator of (I-1) or (I-2), or the protein crystallizing agent of any one of (II-1) to (II-4) into contact with a protein-containing solution; and observing the occurrence of precipitation of the protein.

(IV-2) The method for screening protein crystallization conditions according to (IV-1), comprising the steps of:

using, in a vapor diffusion method, the protein crystallization accelerator of (I-1) or (I-2) as a protein crystallization accelerator, or the protein crystallizing agent of any one of (II-1) to (II-4) as a protein crystallizing agent;

mixing the protein crystallization accelerator or the protein crystallizing agent with the protein-containing solution; and precipitating the protein.

(V) Reagent or Reagent Kit for Screening Protein Crystallization Conditions (V-1) A reagent or a reagent kit for screening protein crystallization conditions, comprising the protein crystallization accelerator of (I-1) or (I-2), or the protein crystallizing agent of any one of (II-1) to (II-4).

(VI) Use of Amino Acid or Amino Acid Derivative as a Protein Crystallization Accelerator or a Protein Crystallizing Agent (VI-1) Use of at least one compound selected from the group consisting of basic amino acids, acidic amino acids, ester derivatives of amino acids, amide derivatives of amino acids, and salts and solvates thereof, as a protein crystallization accelerator or a protein crystallizing agent.

(VI-2) The use according to (VI-1), wherein the basic amino acids are arginine, lysine and ornithine; the acidic amino acids are aspartic acid and glutamic acid; the ester derivatives of amino acids are glycine ethyl ester, lysine ethyl ester, and serine ethyl ester; and the amide derivatives of amino acids are glycinamide, serinamide, threonine amide, argininamide, and prolinamide.

Regardless of its origin, e.g., natural, artificial (a chemical synthesis method, fermentation method, gene recombination method), etc., and production process thereof, the "protein" targeted by the present invention includes peptide, polypeptide, protein, and complex thereof (for example, a complex of (poly)peptide or protein and compound; a complex of (poly) peptide or protein and saccharide; a complex of (poly)peptide or protein and metal; a complex of (poly)peptide or protein and coenzyme, etc.).

The terms "crystallization" and "precipitation of protein crystal" used herein both have the same meaning, indicating producing or growing protein crystals from a protein-containing solution so as to obtain a precipitate of the protein crystals.

The term "a protein-containing solution" refers to a solution in which a target protein for crystallization, or a target protein for which crystallization conditions are defined by a screening method, is dissolved.

Water is a typical example of a solvent usable for protein dissolution, but the use of water containing an organic solvent is not restricted. The protein-containing solution may comprise, in addition to the target protein, a protein solubilizer, which helps in the dissolution of a protein, a stabilizing agent, and the like.

In the present invention, "bringing a protein crystallization accelerator or a protein crystallizing agent into contact with a protein-containing solution" means to place the protein crystallization accelerator or protein crystallizing agent and the protein-containing solution so as to contact each other. The following are representative embodiments: an embodiment in which a protein crystallization accelerator, a protein crystallizing agent or a solution thereof is added to a protein-containing solution; an embodiment in which a protein crystallization accelerator, a protein crystallizing agent or a solution thereof is added to a protein-containing solution and mixed; an embodiment in which the interface of a protein-containing solution is brought into direct or indirect (via gel, dialysis membrane or the like) contact with the interface of a solution containing a protein crystallization accelerator or a protein crystallizing agent; and the like.

Effect of the Invention

Basic amino acids, acidic amino acids, ester derivatives of amino acids, amide derivatives of amino acids, and salts and solvates thereof (hereinafter collectively referred to as "AMINO ACID") usable in the present invention possess properties of accelerating precipitation of protein crystal in a protein-containing solution, and are therefore effectively used for protein crystallization. In view of this, the AMINO ACID used in the present invention is useful as a protein crystallization accelerator.

The AMINO ACID of the present invention possesses, as mentioned above, properties of accelerating protein crystallization. Therefore, the use of the AMINO ACID alone or in combination with a well-known protein crystallizing agent (a precipitant, a pH buffer, etc.) can allow protein crystals to promptly precipitate under a wide range of conditions. In view of this, the AMINO ACID of the present invention can be used singly or in combination with a well-known protein crystallizing agent (a precipitant, a pH buffer, etc.), as a protein crystallizing agent.

According to the protein crystallization accelerator or the protein crystallizing agent above, crystals can be precipitated even with respect to a protein with a slightly low purity. Therefore, the probability (hit rate) of protein crystallization can also be improved.

For this reason, the protein crystallization accelerator of the present invention, which comprises the AMINO ACID, and the protein crystallizing agent of the present invention, which essentially consists of the AMINO ACID or a combination of the AMINO ACID and a well-known protein crystallizing agent, are useful as a screening reagent for finding protein crystallization conditions. Therefore, according to the screening method of the present invention with use of the screening reagent above, protein crystals can be efficiently precipitated under a wide range of conditions, making it possible to promptly and readily find conditions that are optimal for protein crystallization. Further, the screening method of the present invention with use of the screening reagent of the present invention can find the conditions that are optimal for protein crystallization, even with respect to a protein with a slightly low purity.

Recently, a number of companies specializing in protein crystallization or undertaking protein structure analysis have been established internationally. The techniques provided by the present invention are considered useful for protein crystallization, which is a rate-determining step due to its difficulty and indispensability for protein structure analysis, and contribute to, for example, drug discovery based on protein structure analysis.

BEST MODE FOR CARRYING OUT THE INVENTION

I. Protein Crystallization Accelerator

A protein crystallization accelerator of the present invention has a feature of comprising at least one compound selected from the group consisting of basic amino acids, acidic amino acids, ester derivatives of amino acids, amide derivatives of amino acids, and salts and solvates thereof.

Examples of known amino acids include monoamino monocarboxylic acids, such as glycine, valine, alanine, and the like; hydroxy monoamino monocarboxylic acids, such as serine, threonine, and the like; monoamino dicarboxylic acids, such as aspartic acids, glutamic acids, and the like; diamino monocarboxylic acids, such as arginine, lysine, ornithine, and the like; sulfur-containing amino acids, such as methionine, cysteine, and the like; and heterocyclic amino acids, such as proline, histidine, and the like. The basic amino acids targeted by the present invention among the above are diamino monocarboxylic acids, such as arginine, lysine, and ornithine. The targeted acidic amino acids among the amino acids mentioned above are monoamino dicarboxylic acids, such as aspartic acid and glutamic acid. Among the basic amino acids, preferred are lysine and ornithine; and among the acidic amino acids, preferred are glutamic acids.

Ester derivatives of amino acids may be those in which carboxyl group of amino acid is methyl-esterified or ethyl-esterified. Examples thereof include glycine ethyl ester, glycine t-butyl ester, glycine benzyl ester, arginine methyl ester, nitroarginine methyl ester, arginine ethyl ester, lysine methyl ester, lysine ethyl ester, phenylalanine ethyl ester, aspartic acid dimethyl ester, cysteine ethyl ester, serine ethyl ester, threonine ethyl ester, and proline ethyl ester. Preferable examples of ester derivatives of amino acids include glycine ethyl ester, arginine ethyl ester, lysine ethyl ester, serine ethyl ester, and cysteine ethyl ester. Particularly preferred are glycine ethyl ester, lysine ethyl ester, and serine ethyl ester.

Amide derivatives of amino acids may be those in which carboxyl group of amino acid is amidated. Examples thereof include glycinamide, serinamide, threonine amide, argininamide and prolinamide. Preferred among those are prolinamide, glycinamide, and serinamide.

The basic amino acids, acidic amino acids and amino acid derivatives (amino acid ester derivatives, amino acid amide derivatives) may all be in the form of a salt or solvate. Examples of such salts include salts with alkali metals such as sodium, potassium, and the like; salts with alkaline earth metals such as magnesium, calcium, and the like; ammonium salts; salts with inorganic acids such as hydrochloric acid, phosphoric acid, nitric acid, sulfuric acid, sulfurous acid, and the like; and salts with organic acids such as formic acid, acetic acid, propionic acid, butyric acid, oxalic acid, malonic acid, succinic acid, maleic acid, fumaric acid, tartaric acid, and the like. Examples of solvates include hydrates.

The protein crystallization accelerator of the present invention comprises the above basic amino acid, acidic amino acid, amino acid ester derivative and amino acid amide derivative, and salts and solvates thereof (the AMINO ACID). The protein crystallization accelerator of the present invention may comprise a single compound selected from the AMINO ACID above, or a combination of two or more compounds arbitrarily selected from the AMINO ACID.

The protein crystallization accelerator of the present invention possesses properties of accelerating crystal precipitation of the protein dissolved in a solution, and is mainly used for such a purpose. The case where protein is crystallized as a result of the acceleration of crystal precipitation is also considered as utilizing the properties of accelerating crystal precipitation, and is therefore encompassed by the use of the protein crystallization accelerator of the present invention.

The protein crystallization accelerator usually consists of the AMINO ACID; however, as long as the protein crystallization acceleration properties are not impaired, the protein crystallization accelerator may contain another component, in addition to one or more compounds selected from the AMINO ACID. Examples of such components include preservation stabilizers, solubilizers and solubilizing agents, which assist dissolution with respect to a protein-containing solution, and the like. Specific examples thereof include, but are not limited to, glycerol, saccharides, metal ions (for example, $Ca^{++}$, $Mg^{++}$, $Mn^{++}$), salts, buffers, and the like.

The protein crystallization accelerator of the present invention is not particularly limited in form, and may be either a solid (for example, lyophilized form, powder, granules or a tablet) or a liquid. A liquid form is easy to handle, and is therefore preferable. The protein crystallization accelerator in liquid form is usually prepared as an aqueous solution containing the AMINO ACID at a concentration of about 0.1 mM to the saturation.

The protein crystallization accelerator of the present invention is, as mentioned above, used in order to accelerate protein crystallization. In such a use, the protein crystallization accelerator of the present invention may be used in combination with a protein crystallizing agent. Examples of protein crystallizing agents usable herein include those conventionally used as protein crystallizing agents (hereinafter referred to as a "well-known crystallizing agent"). Specific examples thereof include precipitants which have a function of decreasing the solubility of a protein, and pH buffers.

Specific examples of precipitants include salts (for example, chlorides such as sodium chloride, calcium chloride, magnesium chloride, lithium chloride and the like; sulfates such as sodium sulfate, ammonium sulfate, magnesium sulfate, lithium sulfate, cadmium sulfate, and the like; phosphates such as sodium phosphate, potassium phosphate, anhydrous ammonium phosphate, anhydrous potassium phosphate, and the like; hydrogen phosphate salts such as sodium dihydrogen phosphate, potassium dihydrogen phosphate, and the like; nitrates such as sodium nitrate, and the like; acetates, such as sodium acetate, potassium acetate, magnesium acetate, calcium acetate, ammonium acetate, zinc acetate, and the like; citrates such as trisodium citrate, and the like; formates such as sodium formate, potassium formate, and the like; organic acid salts such as potassium sodium tartrate, sodium malonic acid, and the like; and hydrates thereof), water-soluble polymer compounds (for example, polyethylene glycol, polyethylene glycol monoalkyl ether, polyethyleneimine, and the like, which have a molecular weight of about 400 to about 20,000), and organic solvents (for example, 2-methyl-2,4-pentanediol, ethanol, methanol, isopropanol, n-propanol, tert-butanol, dioxane, and the like).

Examples of pH buffers include well-known pH buffers, such as phosphate buffers, citrate buffers, tris buffers, Good's buffers, and the like. Specific examples thereof include sodium acetate trihydrate; potassium phosphate; imidazole; sodium citrate; sodium cacodylate; Good's buffers such as MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, CHES, CAPSO, CAPS, Bis-Tris Propane, and the like; and AMPSO, CABS, glycine, HEPBS, MOBS, TABS, TEA, and the like.

The protein crystallization accelerator of the present invention may be used in combination with, in addition to the well-known crystallizing agent (for example, a precipitant and/or a pH buffer), one or more other adducts, such as a monovalent or divalent salt, an organic solvent, a glycerol, a saccharide, a high molecular compound, a coenzyme, a substrate, a surfactant, and the like.

The well-known crystallizing agent is not limited to the above precipitants, pH buffers and adducts, and may be those disclosed in prior art documents and those used in commercially available protein crystallization screening kits (for example, products of Hampton Research Corp.; Emerald BioStructures, Inc.; Jena Bioscience GmbH; Molecular Dimensions Ltd., etc.).

II. Protein Crystallizing Agent

The protein crystallizing agent of the present invention possesses properties of accelerating precipitation of protein crystals from a protein-containing solution, and is mainly used for this purpose.

The present invention is based on the findings that the aforesaid basic amino acids, acidic amino acids, ester derivatives of amino acids, amide derivatives of amino acids, and salts and solvates thereof (AMINO ACID) not only function as a protein crystallization accelerator, but can also be used alone as a protein crystallizing agent for protein crystallization (see Example 5). Additionally, the AMINO ACID possesses, as mentioned above, the properties of further accelerating protein crystallization when used in combination with another protein crystallizing agent (for example, a well-known crystallizing agent, etc.); therefore, the AMINO ACID may be combined with the other protein crystallizing agent (the well-known crystallizing agent) for use as a protein crystallizing agent. Specifically, the protein crystallizing agent of the present invention encompasses: (1) an embodiment in which the AMINO ACID is used singly, as an active ingredient (a single-use embodiment); and (2) an embodiment in which the AMINO ACID is used in combination with the other protein crystallizing agent (the well-known crystallizing agent), as an active ingredient (a combined-use embodiment).

Examples of the basic amino acids, acidic amino acids, ester derivatives of amino acids, amide derivatives of amino acids, and salts and solvates thereof (AMINO ACID) usable in the protein crystallizing agent of the present invention may be the same as those exemplified in (I) above; and may be, as mentioned in (I), used singly or in a combination of two or more thereof.

Preferable examples of the AMINO ACID, when used in the single-use embodiment in (1) above, include basic amino acids such as lysine, arginine, and ornithine; acidic amino acids such as glutamic acid and aspartic acid; amino acid ester derivatives such as serine ethyl ester, lysine ethyl ester, and glycine ethyl ester; and amino acid amide derivatives such as glycinamide, serinamide, threonine amide, prolinamide, and argininamide.

Examples of protein crystallizing agents (the well-known crystallizing agent) usable in combination with the AMINO ACID when used in the combined-use embodiment (a combined use with the well-known crystallizing agent) listed in (2) above include precipitants which have a function of decreasing the solubility of a protein, and pH buffers.

Examples of usable precipitants may be the same salts, water-soluble polymer compounds, and organic solvents as exemplified in (I) above. Preferable examples of salts include calcium chloride, magnesium chloride, ammonium sulfate, lithium sulfate, phosphoric anhydride sodium, phosphoric anhydride potassium, anhydrous ammonium phosphate, potassium dihydrogen phosphate, magnesium acetate, calcium acetate, ammonium acetate, sodium acetate, zinc acetate, trisodium citrate, sodium formate, potassium formate, potassium sodium tartrate, and hydrates thereof. Preferable examples of water-soluble polymer compounds include polyethylene glycol having a molecular weight of about 400 to about 20,000. Preferable examples of organic solvents include 2-methyl-2,4-pentanediol and isopropanol.

Examples of usable pH buffers may also be the same pH buffers as exemplified in (I) above. Preferable examples include sodium acetate trihydrate, potassium phosphate, imidazole, sodium citrate, sodium cacodylate; and Good's buffers such as HEPES•Na, Tris-HCl, and the like. Such pH buffers may be effectively used to adjust and maintain the pH conditions of a protein-containing solution in a suitable range for crystal precipitation from, for example, pH 3 to 10, and preferably from pH 4 to 9. The pH buffers may be used singly or in a combination of two or more thereof, for the purpose of adjusting the pH conditions as above; if required, an acid or an alkali may be used together therewith.

The AMINO ACID of the present invention may be combined with, in addition to the precipitant and/or pH buffer mentioned above, other adduct, such as a monovalent or divalent salt, an organic solvent, a glycerol, a saccharide, a high molecular compound, a coenzyme, a substrate, a surfactant, and the like, as the well-known crystallizing agent, so as to be used as a protein crystallizing agent.

The well-known crystallizing agent is not limited to the above precipitants, pH buffers and adducts, and may be those disclosed in prior art documents and those used in commercially available protein crystallization screening kits (for example, products from Hampton Research Corp.; Emerald BioStructures, Inc.; Jena Bioscience GmbH; Molecular Dimensions Ltd., etc.).

The protein crystallizing agent of the present invention in the single-use embodiment listed in (1) above usually consists of the AMINO ACID; however, as long as the properties of accelerating protein crystallization are not impaired, the protein crystallizing agent may contain other components, in addition to one or more compounds selected from the AMINO ACID, etc. Examples of such components include preservation stabilizers, solubilizers and solubilizing agents that assist dissolution with respect to a protein-containing solution, and the like. Specific examples include, but are not limited to, glycerol, saccharides, metal ions (for example, $Ca^{++}$, $Mg^{++}$, $Mn^{++}$), salts, buffers, and the like.

In such a case, the protein crystallizing agent of the present invention is not particularly limited in form, and may be either a solid (for example, lyophilized form, powder, granules or a tablet) or a liquid. A liquid form is preferred for its simple usage. The protein crystallizing agent in liquid form is usually prepared as an aqueous solution containing the AMINO ACID at a concentration of about 0.1 mM to the saturation.

The protein crystallizing agent of the present invention in the combined-use embodiment listed in (2) above essentially consists of a combination of the AMINO ACID and at least one component selected from the well-known crystallizing agent mentioned above. The AMINO ACID and at least one component selected from the well-known crystallizing agent mentioned above may be mixed beforehand so as to be included in one package (a combination agent). Alternatively, the AMINO ACID and at least one component selected from the well-known crystallizing agent mentioned above may separately be packaged, so that all the components are mixed at the time of use for the protein crystallization (a set agent). The protein crystallizing agent may contain, as long as the properties of accelerating protein crystallization are not impaired, other components, in addition to the AMINO ACID and the well-known crystallizing agent. Examples of such components include preservation stabilizers, solubilizers and solubilizing agents which assist dissolution with respect to a protein-containing solution, and the like.

The protein crystallizing agent of the present invention prepared as a combination agent is not particularly limited in form, and may be either a solid (for example, lyophilized form, powder, granules or a tablet) or a liquid. A liquid form is easy to handle, and is therefore preferable. The protein crystallizing agent in liquid form is usually prepared as an aqueous solution containing the AMINO ACID at a concentration of about 0.1 mM to the saturation, and having a pH range of 3 to 10, preferably 4 to 9. Additionally, when, as the well-known crystallizing agent, a salt is included, the concentration thereof is, for example, 0.1 M to the saturation; when an organic solvent is included, the concentration is, for example, 1% to 80% (v/v); when a water-soluble polymer is included, the concentration is, for example, 1% to 60% (w/v); and when a pH buffer is included, the concentration is, for example, 5 mM to 0.3 M.

With regards to the protein crystallizing agent of the present invention used as the set agent, the AMINO ACID and at least one component selected from the well-known crystallizing agent are not preliminary mixed, so that the AMINO ACID and at least one component selected from the well-known crystallizing agent are mixed at the time of use. Insofar, the form of each package is not critical.

For example, the AMINO ACID and at least one component selected from the well-known crystallizing agent are identical or different in form, and may be either a solid (for example, lyophilized form, powder, granules or a tablet) or a liquid. The protein crystallizing agent in liquid form is usually prepared as an aqueous solution containing the AMINO ACID at a concentration of about 0.1 mM to the saturation. When, as the well-known crystallizing agent, a salt is included, the concentration thereof is usually 0.1 M to the saturation; when an organic solvent is included, the concentration is usually 1 to 80% (v/v); when a water-soluble polymer is included, the concentration is usually 1 to 60% (w/v); and when a pH buffer is included, the concentration is 5 mM to 0.3 M.

III. Protein Crystallization Method

The method for crystallizing protein of the present invention has a feature of using, in protein crystallization, the protein crystallization accelerator of the present invention as a protein crystallization accelerator, or the protein crystallizing agent of the present invention (the AMINO ACID, or a combination of the AMINO ACID and the well-known crystallizing agent) as a protein crystallizing agent.

Heretofore, as a protein crystallization technique, a batch method, a vapor diffusion method, a liquid-liquid diffusion method and a dialysis method have been employed. The method of the present invention is applicable to any of these techniques.

(III-1) Batch Method

A "batch method" is a method of precipitating a crystal, comprising gradually adding a protein crystallization accelerator or a protein crystallizing agent to a solution containing a target protein for crystallization (a protein-containing solution) so as to bring them into contact with each other; subjecting, when the resulting protein-containing solution becomes slightly cloudy, the protein-containing solution to centrifugal separation so as to remove the insoluble substance; introducing the obtained supernatant into a container such as a small test tube; sealing the container; and subsequently allowing the container to stand still. Alternatively, the method may comprise mixing a protein crystallization accelerator or a protein crystallizing agent with a trace amount (for example, about 1 µl) of a protein-containing solution; and storing the resulting product under the conditions in which evaporation does not occur (for example, storing it as a droplet in a nonvolatile oil). Therefore, the method for crystallizing protein according to the present invention may be applied to the batch method with use of the protein crystallization accelerator of the present invention as the protein crystallization accelerator used in the batch method as above, and the protein crystallizing agent of the present invention as the protein crystallizing agent used in the batch method as above. This method is usually performed under the conditions of −5° C. to 30° C., preferably 0° C. to 25° C.

The concentration of a protein in a protein-containing solution is usually 0.1 to 15% (w/v), preferably 0.3 to 10% (w/v), and more preferably 0.5 to 2% (w/v). To the protein-containing solution, a solubilizer or a solubilizing agent, which helps in the dissolution of protein, a pH buffer, a stabilizing agent, or the like may be added beforehand, in addition to a target protein.

The protein crystallization accelerator or protein crystallizing agent added to the protein-containing solution is preferably in liquid form. The protein crystallization accelerator or protein crystallizing agent usually contains the AMINO ACID at a concentration of 0.1 mM to the saturation, and preferably 50 mM to 2M. When the protein crystallizing agent contains the well-known crystallizing agent (a salt, an organic solvent, a water-soluble polymer, or a pH buffer), the content of a salt is, for example, usually 50 mM to the saturation, and preferably 0.1 to 2 M; the content of an organic solvent is, for example, usually 1 to 80% (v/v), and preferably 5 to 40% (v/v); the content of a water-soluble polymer is, for example, usually 0.1 to 60% (w/v), and preferably 1 to 40% (w/v); and the content of a pH buffer is, for example, usually 5 to 300 mM, and preferably 50 to 200 mM.

The protein crystallization is usually carried out at a pH range of 3 to 10, preferably from 4 to 9. Therefore, a pH buffer is preferably used in such a proportion that the pH of a protein-containing solution is in the range above.

(III-2) Vapor Diffusion Method

A "vapor diffusion method" comprises placing a droplet of a protein-containing solution that is mixed with a protein crystallization accelerator or a protein crystallizing agent into a container containing a buffer solution (reservoir solution) comprising the protein crystallization accelerator or protein crystallizing agent, which have a higher concentration; sealing the resulting container; and subsequently allowing the container to stand still. The method is classified as a hanging drop method or sitting drop method, depending on how the droplet is placed. The hanging drop method comprises, as shown in FIG. 1, placing a small droplet of a protein-containing solution comprising a protein crystallization accelerator or protein crystallizing agent onto a cover glass; turning the cover glass upside-down so that the droplet hangs from the cover glass; and sealing the container by the cover glass intimately attached to the container's circumference. The sitting drop method comprises providing a droplet stand inside a container containing a buffer solution (reservoir solution) comprising the protein crystallization accelerator or protein crystallizing agent, which have a higher concentration; placing a droplet of a protein-containing solution that is mixed with a protein crystallization accelerator or a protein crystallizing agent onto the droplet stand; and sealing the container with a cover glass, or the like. The volume of a droplet of a protein-containing solution is usually adjusted to about $\frac{1}{100}$ of an external liquid volume. The vapor diffusion method is suitable for a broad screening of crystallization conditions, since multiple conditions can be evaluated with a small amount of a protein.

The method for crystallizing protein according to the present invention may be applied to the vapor diffusion method by using the protein crystallization accelerator of the present invention as the protein crystallization accelerator used in the vapor diffusion method as above, and the protein crystallizing agent of the present invention as the protein crystallizing agent used in the vapor diffusion method as above. This method is usually performed under the conditions of 0° C. to 30° C., preferably 4° C. to 25° C.

The concentration of a protein usable herein in a protein-containing solution is usually 0.1 to 15% (w/v), preferably 0.3 to 10% (w/v), and more preferably 0.5 to 2% (w/v).

The reservoir solution containing a protein crystallization accelerator or protein crystallizing agent usually contains the AMINO ACID at a concentration of 0.1 M to the saturation, and preferably 0.2 to 2 M. When the protein crystallizing agent contains the well-known crystallizing agent (a salt, an organic solvent, a water-soluble polymer, or a pH buffer), the content of a salt is, for example, usually 50 mM to the saturation, and preferably 0.1 to 2 M; the content of an organic solvent is, for example, usually 1 to 80% (v/v), and preferably 5 to 40% (v/v); the content of a water-soluble polymer is, for example, usually 0.1 to 60% (w/v), and preferably 1 to 40% (w/v); and the content of a pH buffer is, for example, usually 5 to 300 mM, and preferably 50 to 200 mM.

The concentration of the protein crystallization accelerator or protein crystallizing agent in a droplet of the protein-containing solution is about $^{10}/_{100}$ to about $^{80}/_{100}$ of the reservoir solution. Specifically, the concentration of the AMINO ACID is usually, for example, $^{10}/_{100}$ to $^{80}/_{100}$ of 0.1 mM to the saturation, preferably 1 mM to 1 M. When the protein crystallizing agent contains a well-known crystallizing agent (a salt, an organic solvent, a water-soluble polymer, or pH buffer), the concentration of a salt is usually, for example, $^{10}/_{100}$ to $^{80}/_{100}$ of 50 mM to the saturation, and preferably 0.1 to 3.5 M; the concentration of an organic solvent is usually, for example, $^{10}/_{100}$ to $^{80}/_{100}$ of 1 to 80% (v/v), and preferably 10 to 70% (v/v); the concentration of a water-soluble polymer is usually, for example, $^{10}/_{100}$ to $^{80}/_{100}$ of 0.1 to 60% (w/v), preferably 1 to 40% (w/v); and the concentration of a pH buffer is usually, for example, 5 to 300 mM, and preferably 50 to 200 mM.

The protein crystallization is usually carried out at a pH range of 3 to 10, preferably from 4 to 9. Therefore, a pH buffer is preferably used in such a proportion that the pH of protein-containing solution is in the range above.

(III-3) Liquid-Liquid Diffusion Method or Dialysis Method

A "liquid-liquid diffusion method" (a "free interface method") or a "dialysis method" is a method comprising bringing the interface of a protein-containing solution into direct contact or indirect contact via a gel or a semipermeable membrane with the interface of a buffer solution containing a protein crystallization accelerator or protein crystallizing agent; thereby allowing the protein crystallization accelerator or the protein crystallizing agent to move to the protein-containing solution so as to gradually increase the concentration thereof. These methods can be suitably used to obtain good-quality protein crystals.

The method for crystallizing protein according to the present invention may be applied to the liquid-liquid diffusion method or the dialysis method by using the protein crystallization accelerator of the present invention as the protein crystallization accelerator used in the liquid-liquid diffusion method or dialysis method as above, and the protein crystallizing agent of the present invention as the protein crystallizing agent used in the liquid-liquid diffusion method or dialysis method as above. These methods are usually performed under the conditions of −5° C. to 30° C., preferably 0° C. to 25° C.

The concentration of a protein usable herein in a protein-containing solution is usually 0.1 to 15% (w/v), preferably 0.3 to 10% (w/v), and more preferably 0.5 to 2% (w/v).

With regard to the protein crystallization accelerator or protein crystallizing agent in a buffer solution, the concentration of the AMINO ACID is usually 0.1 mM to the saturation, and preferably 0.2 to 2 M.

When the protein crystallizing agent contains the well-known crystallizing agent (a salt, an organic solvent, a water-soluble polymer, or a pH buffer), the content of a salt is, for example, usually 50 mM to the saturation, and preferably 0.1 to 2 M; the content of an organic solvent is, for example, usually 1 to 80% (v/v), and preferably 5 to 40% (v/v); the content of a water-soluble polymer is, for example, usually 0.1 to 60% (w/v), and preferably 1 to 40% (w/v). Buffer solution containing the protein crystallizing agent may be, for example, an aqueous solution prepared using the pH buffer mentioned above; the concentration thereof is usually, for example, 5 to 300 mM, preferably 50 to 200 mM; and the pH conditions are, for example, pH 3 to 10, preferably pH 4 to 9.

In these methods, the occurrence of crystal precipitation may usually be observed with the naked eye (visual observation); however, for more accuracy, the observation may be carried out using a stereoscopic microscope, an electron microscope, a light microscope, an X-ray diffractometer, or the like. According to the method above, the occurrence of crystal precipitation may be confirmed in a period of several tens of minutes to 30 days, although it varies depending on the type, purity, concentration, etc. of the target protein. Under some conditions, a crystal may be obtained after several months.

The precipitated crystals may be, as necessary, withdrawn from a solution using a capillary, a pipette, or the like; or removed or collected from a solution by means of a small loop or a spatula.

IV. Method for Screening Protein Crystallization Conditions and Reagent Used Therefor The screening method of the present invention comprises finding and determining protein crystallization conditions from a number of conditions (types and concentrations of a protein crystallization accelerator or a protein crystallizing agent, pHs, and temperatures, etc.), and has a feature of using the protein crystallization accelerator or the protein crystallizing agent of the present invention (the AMINO ACID, or a combination of the AMINO ACID and the well-known crystallizing agent), as a protein crystallizing agent. The method is suitably used particularly for a random screening (an initial screening) in the early stage of determining crystallization conditions.

The screening method of the present invention can be performed using any of the foregoing techniques of batch method, vapor diffusion method, liquid-liquid diffusion method and dialysis method. Preferred is a vapor diffusion method (a hanging drop method and a sitting drop method), since multiple conditions may be evaluated with a small amount of a protein.

When a vapor diffusion method is utilized, the screening method of the present invention is performed by placing a droplet of a protein-containing solution that is mixed with the protein crystallization accelerator or protein crystallizing agent of the present invention, into a container containing a buffer solution (an external liquid) comprising the protein crystallization accelerator or protein crystallizing agent, which have a higher concentration; and allowing the container to stand still while the container is sealed. Specifically, the screening method of the present invention is performed by mixing a solution containing a target protein with the protein crystallization accelerator or protein crystallizing agent of the present invention; and placing the protein in the presence of the protein crystallization accelerator or the protein crystallizing agent of the present invention.

Protein crystallization is influenced by parameters such as the purities and concentrations of the target protein; the types and concentrations of a protein crystallization accelerator or protein crystallizing agent used; and, when a plurality of protein crystallization accelerators or protein crystallizing agents is used, the combinations and compositions thereof, pH conditions, and temperature conditions, etc. Therefore, protein crystallization conditions are determined according to the combination of these parameters. Specifically, screening of protein crystallization conditions refers to selecting, from the multiple combinations of the parameters above, the combination of parameters suitable for crystallization of a target protein.

The screening method of the present invention is preferably performed using a microarray or multiple plates, in which a plurality of parameters (purities and concentrations of a target protein; types and concentrations of the protein crystallization accelerator or the protein crystallizing agent of the present invention to be used; and, when a plurality of protein crystallization accelerators or protein crystallizing agents is used, the combinations and compositions thereof, pH conditions, etc.) are provided with the wells. Thereby, optimal conditions may readily and promptly be determined from many of the presumed crystallization conditions, using a small amount of protein samples.

For example, although the protein concentration, one of the parameters, is not limited, it is preferable that the concentration is usually set to several values ranging from 0.1 to 150 mg/ml. The protein-containing solution may contain, in addition to a target protein, a solubilizer, which helps in the dissolution of the protein; a stabilizing agent, such as a reducing agent; and the like.

Regarding the type of protein crystallization accelerator or protein crystallizing agent, one of the parameters, it is preferable to include a variety of embodiments. That is, an embodiment in which one compound selected from basic amino acids, acidic amino acids, ester derivatives of amino acids, amide derivatives of amino acids, and salts and solvates thereof (AMINO ACID) is used; an embodiment in which two or more compounds arbitrarily selected from the AMINO ACID are used in combination; and an embodiment in which one or more compounds selected from the AMINO ACID and one or more component selected from the well-known crystallizing agent (precipitants (salts, water-soluble polymers and organic solvents), pH buffers and other adducts) are used in combination. With respect to the concentrations (concentrations in a reaction mixture) of the AMINO ACID, it is preferable to set several values ranging from, usually, 20 mM to 1 M. When a well-known crystal agent is used together, it is preferable to set several values ranging from, in terms of a salt (a precipitant), usually 50 mM to 2.5 M; in terms of a water-soluble polymer (a precipitant), usually from 0.5 to 40% (w/v); in terms of an organic solvent (a precipitant), usually from 1 to 40% (v/v); and in terms of a pH buffer, usually from 10 mM to 0.2 M.

Since temperature conditions and pH conditions are also required to be included in the protein crystallization conditions, a screening is preferably performed at several different temperature values and pH values. The temperature conditions may be set to several values ranging from, for example, 4° C. to 25° C., and pH conditions may be set to several values ranging from, for example, pH 3 to 9.

Under the conditions with various parameters such as above, a target protein and the protein crystallization accelerator or protein crystallizing agent of the present invention are allowed to stand still in a coexisting manner, until the crystal is precipitated. The sufficient time required for the protein to precipitate is, although it varies depending on the type, concentration and purity of the protein, usually 1 hour to 10 days. If precipitation does not occur even after 30 days or more, the crystallization conditions (a combination of the parameters) can be considered unsuitable for crystallization.

The occurrence of crystal precipitation may usually be observed with the naked eye (visual observation); however, for more accuracy, the observation may be carried out using a stereoscopic microscope, a light microscope, an X-ray diffractometer, or the like. The appearance of crystal precipitation under multiple crystallization conditions may be recorded with, for example, a CCD camera equipped with a microscope, and the obtained image may be processed; thereby, the success or failure of crystallization may be promptly evaluated from a remote location.

When a protein crystal is observed, the conditions (a combination of the parameters) used for the crystal precipitation are determined as crystallization conditions. As required, in order to narrow the obtained conditions down to further detailed protein crystallization conditions, a second stage screening method under protein crystallization conditions, in which the crystallization conditions are adjusted to a narrower range, or a method under the conditions more precisely defined, may be carried out.

Using the thus-determined crystallization conditions, the target protein can be crystallized to form a crystal that is more favorable for an X-ray experiment by means of a protein crystallization technique (a batch method, a vapor diffusion method, a liquid-liquid diffusion method or a dialysis method), which are usually utilized in the related technical field.

According to the screening method of the present invention, which utilizes a vapor diffusion method, a screening of appropriate conditions from multiple protein crystallization conditions can easily be carried out using a small amount of protein; accordingly, this method is useful to easily and promptly determine protein crystallization conditions.

The screening method above can be easily performed by using a screening reagent comprising: the protein crystallization accelerator of the present invention comprising the AMINO ACID mentioned above; the protein crystallization accelerator of the present invention comprising, as an active ingredient, the AMINO ACID mentioned above; or the protein crystallizing agent of the present invention essentially consisting of the AMINO ACID or a combination of the AMINO ACID and a conventionally well-known protein crystallizing agent (the well-known crystallizing agent). Therefore, the present invention provides the foregoing protein crystallization accelerator and the protein crystallizing agent, as a screening reagent.

The screening reagent may be, in addition to the above, in the form of a kit comprising a set of a microarray, a microplate, a cover glass, a specification, a buffer solution, etc., which are used in a screening method.

EXAMPLES

The present invention is described below with reference to experiments and examples; however, the present invention is not limited thereto.

Example 1

Using lysozyme (Seikagaku Corporation) as a protein, various amino acids (glycine, alanine, methionine and ornithine (Wako Pure Chemical Industries, Ltd.), and lysine (Sigma)), amino acid ester derivatives (glycine ethyl ester, lysine ethyl ester and cysteine ethyl ester (Sigma)), and amino acid amide derivatives (glycinamide and prolinamide (Wako Pure Chemical Industries, Ltd.)) were examined for their functions as a protein crystallizing agent or a protein crystallization accelerator.

(1) Process of Experiment

More specifically, a lysozyme solution at a concentration of 25 mg/ml or 50 mg/ml was prepared as a protein solution using a 0.1 M buffer solution (sodium acetate (pH 4.5) or sodium phosphate (pH 6.5)), to which the above-described various amino acids, amino acid ester derivatives, or amino acid amide derivatives were added so that the final concentration was 0.2 M. Using this protein solution, the initial screening for crystallization was performed by a sparse matrix method (J. Jancarik and S.-H. Kim, J. Appl. Cryst. (1991) 24, 409-411). Crystallization was carried out using the hanging drop vapor diffusion method ("Crystallization of protein; For diffraction structural biology", p. 373, Kyoto University Press; supervised by Noriyoshi Sakabe, edited by Shigeo Aihara) in accordance with the procedure described below (see FIG. 1).

A commercially available screening kit, Crystal Screen 1 (Hampton Research), was used for screening. The kit includes the 50 types of solutions shown in Table 1, which were used as reservoir solutions.

TABLE 1

| No. | Salt | | pH Buffer | | pH | Precipitant (I) | | Precipitant (II) |
|---|---|---|---|---|---|---|---|---|
| 1 | 0.02 M | Calcium chloride 2H$_2$O | 0.1 M | Sodium acetate 3H$_2$O | 4.6 | 30% v/v | 2-methyl-2,4-pentanediol | |
| 2 | | | | | | 0.4 M | Sodium potassium tartrate 4H2O | |
| 3 | | | | | | 0.4 M | Ammonium dihydrogen phosphate | |
| 4 | | | 0.1 M | Tris-HCl | 8.5 | 2 M | Ammonium sulfate | |
| 5 | 0.2 M | Trisodium citrate 2H$_2$O | 0.1 M | HEPES-Na | 7.5 | 30% v/v | 2-methyl-2,4-pentanediol | |
| 6 | 0.2 M | Magnesium chloride 6H2O | 0.1 M | Tris-HCl | 8.5 | 30% w/v | Polyethylene glycol 4000 | |
| 7 | | | 0.1 M | Sodium cacodylate | 6.5 | 1.4 M | Sodium acetate 3H2O | |
| 8 | 0.2 M | Trisodium citrate 2H$_2$O | 0.1 M | Sodium cacodylate | 6.5 | 30% v/v | Isopropanol | |
| 9 | 0.2 M | Ammonium acetate | 0.1 M | Trisodium citrate 2H$_2$O | 5.6 | 30% w/v | Polyethylene glycol 4000 | |
| 10 | 0.2 M | Ammonium acetate | 0.1 M | Sodium acetate 3H$_2$O | 4.6 | 30% w/v | Polyethylene glycol 4000 | |
| 11 | | | 0.1 M | Trisodium citrate 2H$_2$O | 5.6 | 1 M | Ammonium dihydrogen phosphate | |
| 12 | 0.2 M | Magnesium chloride 6H$_2$O | 0.1 M | HEPES-Na | 7.5 | 30% v/v | Isopropanol | |

TABLE 1-continued

| No. | Salt | | pH Buffer | | pH | Precipitant (I) | | Precipitant (II) | |
|---|---|---|---|---|---|---|---|---|---|
| 13 | 0.2 M | Trisodium citrate 2H$_2$O | 0.1 M | Tris-HC | 8.5 | 30% v/v | Polyethylene glycol 400 | | |
| 14 | 0.2 M | Calcium chloride 2H$_2$O | 0.1 M | HEPES-Na | 7.5 | 28% v/v | Polyethylene glycol 400 | | |
| 15 | 0.2 M | Ammonium sulfate | 0.1 M | Sodium cacodylate | 6.5 | 30% w/v | Polyethylene glycol 8000 | | |
| 16 | | | 0.1 M | HEPES-Na | 7.5 | 1.5 M | Lithium sulfate H2O | | |
| 17 | 0.2 M | Lithium sulfate H$_2$O | 0.1 M | Tris-HC | 8.5 | 30% w/v | Polyethylene glycol 4000 | | |
| 18 | 0.2 M | Magnesium acetate 4H$_2$O | 0.1 M | Sodium cacodylate | 6.5 | 20% w/v | Polyethylene glycol 8000 | | |
| 19 | 0.2 M | Ammonium acetate | 0.1 M | Tris-HC | 8.5 | 30% v/v | Isopropanol | | |
| 20 | 0.2 M | Ammonium sulfate | 0.1 M | Sodium acetate 3H$_2$O | 4.6 | 25% w/v | Polyethylene glycol 4000 | | |
| 21 | 0.2 M | Magnesium acetate 4H$_2$O | 0.1 M | Sodium cacodylate | 6.5 | 30% v/v | 2-methyl-2,4-pentanediol | | |
| 22 | 0.2 M | Sodium acetate 3H$_2$O | 0.1 M | Tris-HC | 8.5 | 30% w/v | Polyethylene glycol 4000 | | |
| 23 | 0.2 M | Magnesium chloride 6H$_2$O | 0.1 M | HEPES-Na | 7.5 | 30% v/v | Polyethylene glycol 400 | | |
| 24 | 0.2 M | Calcium chloride 2H$_2$O | 0.1 M | Sodium acetate 3H$_2$O | 4.6 | 20% v/v | Isopropanol | | |
| 25 | | | 0.1 M | Imidazole | 6.5 | 1 M | Sodium acetate 3H2O | | |
| 26 | 0.2 M | Ammonium acetate | 0.1 M | Trisodium citrate 2H$_2$O | 5.6 | 30% v/v | 2-methyl-2,4-pentanediol | | |
| 27 | 0.2 M | Trisodium citrate 2H$_2$O | 0.1 M | HEPES-Na | 7.5 | 20% v/v | Isopropanol | | |
| 28 | 0.2 M | Sodium acetate 3H$_2$O | 0.1 M | Sodium cacodylate | 6.5 | 30% w/v | Polyethylene glycol 8000 | | |
| 29 | | | 0.1 M | HEPES-Na | 7.5 | 0.8 M | Sodium potassium tartrate 4H2O | | |
| 30 | 0.2 M | Ammonium sulfate | | | | 30% w/v | Polyethylene glycol 8000 | | |
| 31 | 0.2 M | Ammonium sulfate | | | | 30% w/v | Polyethylene glycol 4000 | | |
| 32 | | | | | | 2 M | Ammonium sulfate | | |
| 33 | | | | | | 4 M | Sodium formate | | |
| 34 | | | 0.1 M | Sodium acetate 3H$_2$O | 4.6 | 2 M | Sodium formate | | |
| 35 | | | 0.1 M | HEPES-Na | 7.5 | 0.8 M | Sodium dihydrogen phosphate | 0.8 M | Potassium dihydrogen phosphate |
| 36 | | | 0.1 M | Tris-HC | 8.5 | 8% w/v | Polyethylene glycol 8000 | | |
| 37 | | | 0.1 M | Sodium acetate 3H$_2$O | 4.6 | 8% w/v | Polyethylene glycol 4000 | | |
| 38 | | | 0.1 M | HEPES-Na | 7.5 | 1.4 M | Trisodium citrate 2H2O | | |
| 39 | | | 0.1 M | HEPES-Na | 7.5 | 2% v/v | Polyethylene glycol 400 | 2 M | Ammonium sulfate |
| 40 | | | 0.1 M | Trisodium citrate 2H$_2$O | 5.6 | 20% v/v | Isopropanol | 20% w/v | Polyethylene glycol 4000 |
| 41 | | | 0.1 M | HEPES-Na | 7.5 | 10% v/v | Isopropanol | 20% w/v | Polyethylene glycol 4000 |
| 42 | 0.05 M | Potassium dihydrogen phosphate | | | | 20% w/v | Polyethylene glycol 8000 | | |
| 43 | | | | | | 30% w/v | Polyethylene glycol 1500 | | |
| 44 | | | | | | 0.2 M | Potassium formate | | |
| 45 | 0.2 M | Zinc acetate 2H$_2$O | 0.1 M | Sodium cacodylate | 6.5 | 18% w/v | Polyethylene glycol 8000 | | |
| 46 | 0.2 M | Calcium acetate H$_2$O | 0.1 M | Sodium cacodylate | 6.5 | 18% w/v | Polyethylene glycol 8000 | | |
| 47 | | | 0.1 M | Sodium acetate 3H$_2$O | 4.6 | 2 M | Ammonium sulfate | | |
| 48 | | | 0.1 M | Tris-HC | 8.5 | 2 M | Ammonium dihydrogen phosphate | | |
| 49 | 1 M | Lithium sulfate H$_2$O | | | | 2% w/v | Polyethylene glycol 8000 | | |
| 50 | 0.5 M | Lithium sulfate H$_2$O | | | | 15% w/v | Polyethylene glycol 4000 | | |

Crystallization Procedure: Hanging Drop Vapor Diffusion Method (FIG. 1)

Procedure 1: A reservoir solution (500 μl) of each composition shown in Table 1 is put in a beaker, and 1 μl of protein solution (lysozyme solution at a concentration of 25 or 50 mg/ml) is placed on a cover glass.

Procedure 2: 1 μl of reservoir solution is taken out from the beaker.

Procedure 3: The taken reservoir solution (1 μl) is mixed with the protein solution (1 μl) on the cover glass.

Procedure 4: The cover glass is reversed and tightly covers the top of the beaker for sealing so that the droplet of the protein solution is hung towards the inside of the beaker.

Procedure 5: The beaker is allowed to stand at 20° C. in this state, and the presence or absence of crystal precipitation is observed.

Additionally, the same procedure was performed as a control experiment (control) using, in place of the protein solution used above, a lysozyme solution at a concentration of 25 mg/ml or 50 mg/ml that was prepared by means of a 0.1 M buffer solution free from amino acids and amino acid derivatives (sodium acetate (pH 4.5) or sodium phosphate (pH 6.5)).

The presence or absence of crystal precipitation was determined by observing the precipitates produced in the protein solutions through an optical microscope. Precipitates having a sharp and clear shape (crystal edge) and high transparency were determined to denote the "presence of crystal precipitation".

(2) Experimental Results

Tables 2 and 3 show the results of crystallization under different pH conditions (pH 4.5 and pH 6.5). The numbers indicated in each table represent the number of the solution that resulted in crystal deposition, among the 50 reservoir solutions used, and the % next to the numbers represents the success rate of crystallization (hit ratio). In addition, FIG. 2 illustrates these results in graph form.

TABLE 2

| Additive | Buffer: 0.1 M Na phosphate (pH 6.5) | | Buffer: 0.1 M CH₃COONa (pH 4.5) | |
|---|---|---|---|---|
| | Crystal Screen No. of success | Success rate of crystallization (%) | Crystal Screen No. of success | Success rate of crystallization (%) |
| Control | 6, 7, 9, 15, 20, 29, 34, 40, 41, 43, 45, 48 | 24.0% | 7, 9, 22, 28, 29, 34, 35, 48 | 16.0% |
| Gly | 7, 9, 22, 28, 29, 31, 34, 35, 40, 41, 48 | 22.0% | 7, 9, 29, 34, 35, 38, 40, 48 | 16.0% |
| Ala | 6, 7, 9, 15, 17, 20, 22, 29, 30, 34, 40, 41, 48 | 26.0% | 6, 7, 9, 15, 17, 20, 22, 29, 34, 38, 40, 48 | 24.0% |
| Met | 6, 7, 9, 12, 22, 28, 29, 34, 40, | 18.0% | 7, 9, 22, 34 | 8.0% |

TABLE 3

| Additive | Buffer: 0.1 M Na phosphate (pH 6.5) | | Buffer: 0.1 M CH₃COONa (pH 4.5) | |
|---|---|---|---|---|
| | Crystal Screen No. of success | Success rate of crystallization (%) | Crystal Screen No. of success | Success rate of crystallization (%) |
| Lys | 6, 7, 9, 10, 15, 16, 17, 20, 22, 25, 28, 29, 30, 31, 34, 35, 38, 39, 41, 48, | 42.0% | 6, 7, 9, 10, 15, 17, 20, 22, 25, 28, 29, 30, 31, 34, 35, 38, 39, 40, 41, 48 | 40.0% |
| Orn | 6, 7, 9, 10, 15, 17, 20, 22, 25, 28, 29, 30, 31, 34, 35, 38, 39, 40, 41, 48 | 40.0% | 6, 7, 9, 15, 16, 17, 20, 22, 29, 30, 31, 34, 35, 38, 39, 40, 48 | 34.0% |
| GlyEE | 6, 7, 9, 15, 17, 20, 21, 22, 25, 28, 29, 30, 31, 34, 35, 38, 39, 40, 48, 50 | 40.0% | 6, 7, 9, 15, 17, 20, 22, 28, 29, 30, 31, 34, 35, 38, 40, 48 | 32.0% |
| ArgEE | 6, 17, 22, 34, 38, 45 | 12.0% | 7, 9, 15, 17, 22, 28, 29, 30, 31, 34, 35, 38, 39 | 26.0% |
| LysEE | 6, 7, 9, 10, 12, 15, 17, 20, 22, 25, 28, 29, 30, 31, 34, 35, 38, 39, 40, 48 | 40.0% | 6, 7, 9, 10, 15, 17, 18, 20, 22, 25, 28, 29, 30, 31, 34, 35, 38, 39, 40, 48 | 40.0% |
| CysEE | 6, 7, 8, 9, 15, 20, 22, 25, 28, 29, 30, 31, 34, 38, 39, 40 | 32.0% | 5, 7, 9, 11, 12, 13, 15, 17, 20, 26, 28, 29, 34, 38, 40 | 30.0% |

Tables 4 and 5 show the results of crystallization at pH 4.5 under different protein concentration conditions (25 mg/ml and 50 mg/ml). Similar to Tables 2 and 3, the numbers indicated in each table represent the number of the solution that resulted in crystal deposition, among the 50 reservoir solutions used, and the % next to the numbers represents the success rate of crystallization (hit ratio). In addition, FIG. 3 illustrates these results in graph form.

TABLE 4

| Additive | Buffer: 0.1 M CH$_3$COONa (pH 4.5) 25 mg/ml lysozyme | | Buffer: 0.1 M CH$_3$COONa (pH 4.5) 50 mg/ml lysozyme | |
|---|---|---|---|---|
| | Crystal Screen No. of success | Success rate of crystallization (%) | Crystal Screen No. of success | Success rate of crystallization (%) |
| control | 9, 22, 25, 29, 34, 35 | 12.0% | 2, 6, 7, 9, 10, 22, 28, 29, 34, 35, 41 | 22.0% |
| Arg | 17, 34, 35, 48 | 8.0% | 6, 7, 9, 10, 15, 20, 22, 24, 28, 29, 30, 31, 34, 35, 38, 39, 42, 48 | 36.0% |
| Lys | 6, 7, 17, 22, 29, 30, 34, 35, 40, 48 | 20.0% | 7, 8, 9, 15, 17, 20, 22, 25, 29, 30, 31, 34, 35, 38, 48 | 30.0% |

TABLE 5

| Additive | Buffer: 0.1 M CH$_3$COONa (pH 4.5) 25 mg/ml lysozyme | | Buffer: 0.1 M CH$_3$COONa (pH 4.5) 50 mg/ml lysozyme | |
|---|---|---|---|---|
| | Crystal Screen No. of success | Success rate of crystallization (%) | Crystal Screen No. of success | Success rate of crystallization (%) |
| Orn | 6, 7, 9, 15, 16, 17, 20, 22, 29, 30, 31, 34, 35, 38, 39, 40, 48 | 34.0% | 2, 6, 7, 9, 10, 11, 15, 17, 20, 22, 25, 28, 29, 30, 31, 34, 35, 38, 39, 40, 48, 50 | 44.0% |
| GlyEE | 6, 7, 9, 15, 17, 20, 22, 28, 29, 30, 31, 34, 35, 38, 40, 48 | 32.0% | 6, 7, 9, 10, 13, 15, 17, 18, 20, 22, 23, 25, 28, 29, 30, 31, 34, 35, 38, 39, 40, 48 | 44.0% |
| GlyAmd | 7, 9, 10, 15, 17, 20, 22, 28, 29, 30, 31, 34, 35, 38, 39, 40 | 32.0% | 6, 7, 9, 10, 11, 15, 17, 20, 22, 23, 25, 28, 29, 30, 31, 34, 35, 38, 39, 40, 41, 48, 50 | 46.0% |
| LysEE | 6, 7, 9, 10, 15, 17, 18, 20, 22, 25, 28, 29, 30, 31, 34, 35, 38, 39, 40, 48 | 40.0% | 2, 6, 7, 9, 10, 11, 13, 14, 15, 16, 17, 18, 20, 22, 23, 25, 28, 29, 30, 31, 35, 39, 40, 41, 46, 48, 49, 50 | 56.0% |
| CysEE | 5, 7, 9, 11, 12, 13, 15, 17, 20, 26, 28, 29, 34, 38, 40 | 30.0% | 2, 5, 6, 7, 9, 10, 11, 15, 17, 20, 22, 28, 29, 30, 31, 34, 35, 38, 40, 46, 48 | 42.0% |

Table 6 shows the results of crystallization at pH 6.5 under different protein concentration conditions (25 mg/ml and 50 mg/ml). Similar to Tables 2, 3, 4 and 5, the numbers indicated in each table represent the number of the solution that resulted in crystal deposition, among the 50 reservoir solutions used, and the % next to the numbers represents the success rate of crystallization (hit ratio). In addition, FIG. 4 illustrates these results in graph form.

show that these amino acids or amino acid derivatives function as a protein crystallizing agent or protein crystallization accelerator.

Example 2

Using lysozyme (Seikagaku Corporation) as a protein, various amino acids (glycine, serine, aspartic acid, glutamic

TABLE 6

| | 25 mg/ml lysozyme | | 50 mg/ml lysozyme | |
|---|---|---|---|---|
| Additive | Crystal Screen No. of success | Success rate of crystallization (%) | Crystal Screen No. of success | Success rate of crystallization (%) |
| control | 6, 7, 9, 15, 20, 29, 34, 40, 41, 43, 45, 48 | 24.0% | 2, 6, 7, 9, 10, 13, 15, 17, 20, 22, 25, 28, 29, 30, 31, 34, 35, 38, 39, 40, 41, 43, 45, 48 | 48.0% |
| Lys | 6, 7, 9, 15, 17, 22, 25, 28, 29, 30, 31, 34, 35, 38, 39, 40, 41, 48 | 36.0% | 6, 7, 9, 10, 15, 17, 18, 20, 22, 24, 25, 28, 29, 30, 31, 34, 35, 38, 39, 40, 41, 45, 48 | 46.0% |
| Orn | 6, 7, 9, 10, 15, 17, 20, 22, 25, 28, 29, 30, 31, 34, 35, 38, 39, 40, 41, 48 | 40.0% | 2, 6, 7, 9, 10, 11, 13, 15, 17, 18, 20, 22, 23, 25, 28, 29, 30, 31, 34, 35, 38, 39, 40, 41, 46, 48, 50 | 54.0% |
| GlyEE | 6, 7, 9, 15, 17, 20, 21, 22, 25, 28, 29, 30, 31, 34, 35, 38, 39, 40, 48, 50 | 40.0% | 6, 7, 9, 10, 13, 15, 17, 18, 20, 22, 25, 28, 29, 30, 31, 34, 35, 38, 39, 40, 46, 48, 50 | 46.0% |
| LysEE | 6, 7, 9, 10, 12, 15, 17, 20, 22, 25, 28, 29, 30, 31, 34, 35, 38, 39, 40, 48 | 40.0% | 2, 6, 7, 9, 10, 11, 12, 13, 15, 17, 18, 20, 22, 23, 25, 28, 29, 30, 31, 34, 35, 38, 39, 40, 41, 46, 48, 50 | 56.0% |
| CysEE | 6, 7, 8, 9, 15, 20, 22, 25, 28, 29, 30, 31, 34, 38, 39, 40 | 32.0% | 6, 7, 8, 9, 10, 11, 13, 15, 17, 18, 20, 22, 25, 28, 29, 30, 31, 34, 35, 38, 39, 40, 41, 48 | 48.0% |
| GlyAmd | 6, 7, 9, 10, 15, 16, 17, 20, 22, 25, 28, 29, 30, 31, 34, 35, 38, 39, 41, 46, 48 | 42.0% | 6, 7, 9, 10, 13, 15, 17, 18, 20, 22, 23, 25, 28, 29, 30, 31, 34, 35, 38, 39, 40, 41, 43, 44, 46, 48, 50 | 54.0% |
| ProAmd | 6, 7, 9, 10, 15, 17, 20, 21, 22, 25, 28, 29, 30, 31, 34, 35, 38, 39, 40, 41, 43, 45, | 44.0% | 6, 7, 9, 10, 13, 15, 17, 18, 20, 23, 25, 28, 29, 30, 31, 35, 38, 39, 40, 42, 43, 45, 46, 48, | 48.0% |

In case the success rate of crystallization when using the amino acids or amino acid derivatives is larger than that of the control experiment (control: left end of each graph), it is determined that the protein crystallization is promoted by the addition of the amino acid or amino acid derivative.

The results in FIG. 2 revealed that the crystallization was promoted by using lysine, ornithine, glycine ethyl ester, lysine ethyl ester, cysteine ethyl ester and glycinamide, regardless of the pH level. Further, FIG. 3 showed that in the case of lysozyme at a concentration of 25 mg/ml, the crystallization was facilitated by using lysine, ornithine, glycine ethyl ester, lysine ethyl ester, cysteine ethyl ester and glycinamide; whereas in the case of lysozyme at a concentration of 50 mg/ml, the crystallization was facilitated by using arginine, lysine, ornithine, glycine ethyl ester, lysine ethyl ester, cysteine ethyl ester and glycinamide.

Moreover, FIG. 4 indicated that when using lysozyme at a concentration of 25 mg/ml, the crystallization was facilitated by using ornithine, glycine ethyl ester, lysine ethyl ester, cysteine ethyl ester, glycinamide and prolinamide; whereas when using lysozyme at a concentration of 50 mg/ml, the crystallization was facilitated by using ornithine, glycine ethyl ester, lysine ethyl ester, cysteine ethyl ester, glycinamide and prolinamide.

These results demonstrate that although the type of effective additives varies depending on the pH level, protein concentration and other conditions, the addition of the basic amino acids (arginine, lysine, and ornithine, amino acid ester derivatives or amino acid amide derivatives to the protein solution promotes crystallization, which means that the success rate of crystallization is enhanced. That is, these results acid, arginine and ornithine (Wako Pure Chemical Industries, Ltd.), and lysine (Sigma)) and amino acid derivatives (glycine ethyl ester (Sigma) and glycinamide (Wako Pure Chemical Industries, Ltd.)) were examined for their functions as a protein crystallizing agent or protein crystallization accelerator.
(1) Process of Experiment Using, as a protein solution, a lysozyme solution at a concentration of 25 mg/ml that was prepared by means of a 0.1 M buffer solution (sodium dihydrogen phosphate (pH 6.5)), and using an amino acid- or amino acid derivative-containing solution of the following composition as a reservoir solution, the presence or absence of crystal precipitation was observed by the same procedure as the hanging drop vapor diffusion method used in Example 1 (Procedures 1 to 5).
Composition of Reservoir Solution Buffer solution: 0.1 M sodium dihydrogen phosphate (pH 6.5)

Precipitant: 2.0 M to 0.1 M sodium chloride

Additives: 0.1 M to 1.0 M various amino acids or amino acid derivatives

Moreover, the same procedure was performed as a control experiment (control) using, as a reservoir solution, a solution containing only the above buffer solution (0.1 M sodium dihydrogen phosphate (pH 6.5)) and precipitant (2.0 M to 0.1 M sodium chloride), rather than the additives (amino acids and amino acid derivatives).
(2) Experimental Results FIGS. 5, 6 and 7 show the results. FIG. 5 indicates the result that was observed on the 9th day from the beginning of crystallization, and FIG. 6 indicates the result that was observed on the 3rd day from the beginning of crystallization.

FIG. 7 shows the result of crystallization at a protein concentration of 50 mg/ml. The vertical axis of each figure indicates the concentration of the precipitant (NaCl) used for crystallization. The bar obtained when adding various amino acids or amino acid derivatives, which is longer than that obtained in the control experiment (control; left end in each figure), indicates that crystallization is promoted with the amino acid or amino acid derivative, expanding the concentration range of the precipitant for precipitating crystals; namely, widening the range of crystallization conditions.

As shown in FIG. 5, the addition of the amino acids (acidic amino acids, i.e., arginine and lysine; and basic amino acids, i.e., aspartic acid and glutamic acid) other than glycine and serine, and the amino acid ester derivative (glycine ethyl ester) provided different results from the control. More specifically, it was confirmed that arginine and glycine ethyl ester promoted protein crystallization in a high-concentration precipitant-containing solution (highly supersaturated solution), while the other amino acids (lysine, aspartic acid and glutamic acid) and glycine ethyl ester promoted protein crystallization in a low-concentration precipitant-containing solution (low supersaturated solution).

This shows that crystals can be precipitated under a wide range of conditions by using the above amino acids (basic amino acids, i.e., arginine and lysine; and acidic amino acids, i.e., aspartic acid and glutamic acid) or amino acid ester derivatives in combination with a known precipitant. In other words, it was found that the use of these amino acids or amino acid ester derivatives promotes crystallization, and thereby crystals are precipitated even under conditions where no crystallization occurs when using a conventional precipitant (control), enhancing the success rate of crystallization.

FIG. 6 shows the result of the crystallization on the 3rd day from the beginning of crystallization. Even under a condition where no crystallization occurred through the use of a conventional precipitant (control), crystals were precipitated by using the above-described amino acids or amino acid ester derivatives. Further, from the fact that this result is not much different from that of the 9th day from the beginning of crystallization (FIG. 5), the addition of the above amino acids or amino acid ester derivatives results in a reduction of the time necessary for the crystal precipitation.

Further, as shown in FIG. 7, the addition of the amino acids (basic amino acids, i.e., arginine, lysine and ornithine; and acidic amino acids, i.e., aspartic acid and glutamic acid) other than glycine and serine, the amino acid ester derivative (glycine ethyl ester), and the amino acid amide derivative (glycinamide) provided different results from the control. More specifically, it was confirmed that arginine, glycine ethyl ester, and glycinamide promoted protein crystallization in a high-concentration precipitant-containing solution (highly supersaturated solution), while the other amino acids (lysine, aspartic acid, glutamic acid, and ornithine), glycine ethyl ester, and glycinamide promoted protein crystallization in a low-concentration precipitant-containing solution (low supersaturated solution).

These results reveal that crystallization is promoted by adding the above amino acids (basic amino acids such as arginine, lysine and ornithine; and acidic amino acids such as aspartic acid and glutamic acid), amino acid ester derivatives, or amino acid amide derivatives to a protein solution during crystallization, thereby allowing crystal precipitation under a wide range of conditions and in a short period of time. That is, these results imply that the success rate of protein crystallization can be enhanced by using basic amino acids, acidic amino acids, amino acid ester derivatives, or amino acid amide derivatives in combination with a known protein crystallizing agent in the initial screening of protein crystallization.

Example 3

Using lysozyme (Seikagaku Corporation) as a protein, various amino acids (glycine, arginine and ornithine (Wako Pure Chemical Industries, Ltd.), and lysine (Sigma)), amino acid ester derivatives (glycine ethyl ester, serine ethyl ester and lysine ethyl ester (Sigma)), and amino acid amide derivatives (glycinamide, serinamide, threonine amide, prolinamide and argininamide (Wako Pure Chemical Industries, Ltd.)) were examined for their functions as a protein crystallizing agent or a protein crystallization accelerator in the same manner as in Example 2.

FIG. 8 shows the results observed on the 2nd day from the beginning of crystallization at a lysozyme concentration of 50 mg/ml. The vertical axis of the figure indicates the concentration of the precipitant (NaCl) used for crystallization. The bar obtained when adding various amino acids or amino acid derivatives, which is longer than that obtained in the control experiment (control; left end in each figure) or is shifted from the range of the control bar, indicates that crystallization is promoted with the amino acid or amino acid derivative, expanding the concentration range of the precipitant for precipitating crystals; namely, widening the range of crystallization conditions.

As shown in FIG. 8, the addition of the amino acids (basic amino acids, i.e., arginine, lysine and ornithine) other than glycine, the amino acid ester derivatives (glycine ethyl ester, serine ethyl ester and lysine ethyl ester), and the amino acid amide derivatives (glycinamide, serinamide, threonine amide, prolinamide and argininamide) provided different results from the control. More specifically, it was confirmed that arginine, glycine ethyl ester, serine ethyl ester, lysine ethyl ester, glycinamide, threonine amide, prolinamide and argininamide promoted protein crystallization in a high-concentration precipitant-containing solution (highly supersaturated solution), while the other amino acids (lysine and ornithine) and glycine ethyl ester, serine ethyl ester, lysine ethyl ester, glycinamide and prolinamide promoted protein crystallization in a low-concentration precipitant-containing solution (low supersaturated solution).

This shows that crystals can be precipitated under a wide range of conditions by using the above amino acids (basic amino acids, i.e., arginine, lysine and ornithine), amino acid ester derivatives, or amino acid amide derivatives in combination with a known precipitant. In other words, it was found that the use of these amino acids, amino acid ester derivatives, or amino acid amide derivatives promote crystallization, and thereby crystals are precipitated even under conditions where no crystallization occurs when using a conventional precipitant (control), enhancing the success rate of crystallization.

Example 4

The crystallization of lysozyme using ammonium sulfate as a precipitant is considered extremely difficult (Acta Cryst. (1997) D53, 759-797; and Acta Cryst. (1994) D50, 366-369)). Hence, under the condition where ammonium sulfate was used as a precipitant, whether crystals of lysozyme would be precipitated was examined when the acidic amino acid (glutamic acid), basic amino acid (arginine, lysine or ornithine), amino acid ester derivative (glycine ethyl ester) or amino acid amide derivative (glycinamide) was added.

(1) Process of Experiment

Using, as a protein solution, a 0.1 M buffer solution (sodium dihydrogen phosphate (pH 6.5)) that was prepared by means of a lysozyme solution at a concentration of 100 mg/ml or 150 mg/ml, and using an amino acid- or amino acid derivative-containing solution of the following composition as a reservoir solution, the presence or absence of crystal precipitation was observed by the same procedure as the hanging drop vapor diffusion method used in Example 1 (Procedures 1 to 5).

Composition of Reservoir Solution

Buffer solution: 0.1 M sodium dihydrogen phosphate (pH 6.5)

Precipitant: 1.5 M to 0.1 M ammonium sulfate

Additives: 0.1 M to 1.0 M various amino acids or amino acid derivatives

Moreover, the same procedure was performed as a control experiment (control) using, as a reservoir solution, a solution containing only the above buffer solution (0.1 M sodium dihydrogen phosphate (pH 6.5)) and precipitant (1.5 M to 0.1 M ammonium sulfate), rather than the additives (amino acids and amino acid derivatives).

(2) Experimental Results

FIG. 9 (100 mg/ml lysozyme) and FIG. 10 (150 mg/ml lysozyme) show the results three weeks after the beginning of crystallization. The vertical axis of the figure indicates the concentration of the precipitant (ammonium sulfate) used for crystallization. As shown in FIGS. 9 and 10, no crystals were precipitated in the control experiment (control; left end) in which none of basic amino acids, acidic amino acids, and amino acid derivatives was used; however, when using basic amino acids, acidic amino acids, amino acid ester derivatives or amino acid amide derivatives, particularly glutamic acid, arginine, lysine, ornithine, glycine ethyl ester, or glycinamide, crystals were precipitated in the presence of the precipitant (ammonium sulfate). This result indicates that crystallization is promoted with basic amino acids, acidic amino acids, amino acid ester derivatives, and amino acid amide derivatives, allowing for crystallization of lysozyme using ammonium sulfate as a precipitant, which was traditionally considered to be difficult; in addition, the use of basic amino acids, acidic amino acids, amino acid ester derivatives, and amino acid amide derivatives expands the variety of precipitants efficiently usable in protein crystallization, which means that the range of crystallization conditions usable in the initial screening of protein crystallization can be extended.

In the documents (Acta Cryst. (1997) D53, 759-797; and Acta Cryst. (1994) D50, 366-369) described above, lysozyme crystallization using ammonium sulfate as a precipitant was finally successful after purifying commercially available lysozyme to obtain high-purity lysozyme. However, according to the method of the present invention, crystallization of commercially available lysozyme using ammonium sulfate was successful only by adding the above-described amino acids or amino acid derivatives to the lysozyme, as stated above. This indicates that even proteins with poor purity can be successfully crystallized by the use of the above amino acids or amino acid derivatives.

Example 5

Using hemoglobin (Sigma) as a protein, various amino acids (proline, serine, aspartic acid and glutamic acid (Wako Pure Chemical Industries, Ltd.)) were examined for their functions as a protein crystallizing agent or a protein crystallization accelerator.

(1) Process of Experiment

Using, as a protein solution, a 4% (w/v) hemoglobin solution that was prepared by means of a 0.1 M buffer solution (sodium dihydrogen phosphate (pH 6.5)), and using an amino acid-containing solution of the following composition as a reservoir solution, the presence or absence of crystal precipitation was observed by the same procedure as the hanging drop vapor diffusion method used in Example 1 (Procedures 1 to 5).

Composition of Reservoir Solution

Buffer solution: 0.1 M sodium dihydrogen phosphate (pH 6.5)

Precipitant: 12.5% (w/v) to 25.0% (w/v) polyethylene glycol 3350

Additives: 0.2 M to 1.0 M various amino acids

Moreover, the same procedure was performed as a control experiment (control) using, as a reservoir solution, a solution containing only the above buffer solution (0.1 M sodium dihydrogen phosphate (pH 6.5)) and precipitant (12.5% (w/v) to 25.0% (w/v) polyethylene glycol), rather than the additives (amino acids).

(2) Experimental Results

FIG. 11 shows the result on the 3rd day after the beginning of crystallization. The vertical axis of the figure represents the concentration of the precipitant (PEG) used for crystallization. The concentration range of the polyethylene glycol 3350 examined was lower than 25% (w/v). Accordingly, the bar obtained when adding various amino acids, which extends downwardly longer than that obtained in the control experiment (control: left end in each figure), indicates that crystallization is promoted with the amino acid, expanding the concentration range of the precipitant (PEG) for precipitating crystals; namely, widening the range of crystallization conditions. This result showed that the use of acidic amino acids, i.e., aspartic acid or glutamic acid, widens the range of crystallization conditions when using polyethylene glycol as a precipitant.

FIG. 12 shows micrographs of crystals that were precipitated through the use of aspartic acid or glutamic acid (eyepiece lens×10, objective lens×4). In addition, a micrograph of a crystal that was precipitated through the use of arginine is also provided. The micrograph represented by "no additive" shows the protein crystal obtained in the control experiment (control), which could not be used in the X-ray diffraction experiment due to the overlapping of small crystals (originally, 4% (w/v) hemoglobin and, as a precipitant, 17.5% (w/v) PEG 3350 were used). On the other hand, the protein crystals obtained by adding aspartic acid, glutamic acid, or arginine were all single crystals that had good quality, allowing them to be suitably used in the X-ray diffraction experiment. This suggested that acidic amino acids can not only extend the range of crystallization conditions, but also improve the quality of the crystals.

Example 6

Using ribonuclease A (Worthington) as a protein, various amino acids (alanine, glutamic acid and ornithine (Wako Pure Chemical Industries, Ltd.), and aspartic acid and lysine (Sigma)), and amino acid derivative (glycine ethyl ester) were examined for their functions as a protein crystallizing agent or a protein crystallization accelerator.

(1) Process of Experiment

Using, as a protein solution, 25 mg/ml ribonuclease A solution that was prepared by means of a 0.1 M buffer solution (sodium acetate (pH 6.0)), and using an amino acid-containing solution of the following composition as a reservoir solution, the presence or absence of crystal precipitation was observed by the same procedure as the hanging drop vapor diffusion method used in Example 1 (Procedures 1 to 5).

Composition of Reservoir Solution

Buffer solution: 0.1 M sodium acetate (pH 6.0)

Precipitant: 35% (w/v) ammonium sulfate

Additives: 0.5 M various amino acids or amino acid derivatives

Moreover, the same procedure was performed as a control experiment (control) using, as a reservoir solution, a solution containing only the above buffer solution (0.1 M sodium acetate (pH 6.0)) and precipitant (35% (w/v) ammonium sulfate), rather than the additives (amino acids).

(2) Experimental Results

FIG. 13 shows micrographs of crystals that were precipitated through the use of aspartic acid or glycine ethyl ester (eyepiece lens×10, objective lens×4). The micrograph represented by "no additive" shows the protein crystal obtained in the control experiment (control), in which no crystal precipitation was observed, but only amorphous precipitates were observed. Meanwhile, protein crystals of good quality were obtained by adding aspartic acid or glycine ethyl ester. In the document (Protein Sci. (2002) 11(1). 72), ribonuclease A was successfully crystallized by using ammonium sulfate as a precipitant. However, depending on protein purity, protein crystallization often does not occur under previously reported crystallization conditions. According to the method of the present invention, however, as stated above, the crystallization of commercially available ribonuclease A using ammonium sulfate was successful only by adding the above-mentioned amino acid or amino acid derivative to the ribonuclease A, which is not crystallized under existing crystallization conditions and is considered to have a slight purity problem. This means that even proteins with insufficient purity can be successfully crystallized by the use of the above amino acids or amino acid derivatives. This suggested that particularly acidic amino acids can enhance the crystallization of proteins even with insufficient purity.

Example 7

Using lysozyme (Seikagaku Corporation) as a protein, various amino acids (glutamic acid, ornithine, arginine and aspartic acid (Wako Pure Chemical Industries, Ltd.), and lysine (Sigma)), amino acid ester derivatives (glycine ethyl ester and arginine ethyl ester (Sigma)), and amino acid amide derivative (glycinamide (Wako Pure Chemical Industries, Ltd.)) were examined for their function as a protein crystallizing agent, when used singularly.

(1) Process of Experiment

Using, as a protein solution, a lysozyme solution at a concentration of 50 mg/ml, 100 mg/ml, or 150 mg/ml that was prepared by means of a 0.1 M buffer solution (sodium dihydrogen phosphate (pH 6.5)), and using an amino acid- or amino acid derivative-containing solution of the following composition as a reservoir solution, the presence or absence of crystal precipitation was observed by the same procedures as the hanging drop vapor diffusion method used in Example 1 (Procedures 1 to 5).

Composition of Reservoir Solution

Buffer solution: 0.1 M sodium dihydrogen phosphate (pH 6.5)

Additives: 0.75 M to 2.0 M various amino acids or amino acid derivatives (2) Experimental Results FIG. 14 shows the result on the 14th day after the beginning of crystallization. Crystals were precipitated when adding the amino acids (lysine, arginine, ornithine, aspartic acid and glutamic acid), amino acid ester derivatives (arginine ethyl ester and glycine ethyl ester), or amino acid amide derivative (glycinamide). This result demonstrates that the acidic amino acids (aspartic acid and glutamic acid), basic amino acids (arginine, lysine and ornithine), amino acid amide derivative (glycinamide), and amino acid ester derivatives (arginine ethyl ester and glycine ethyl ester) independently crystallize protein, and are thus useful as protein crystallizing agents.

Figure 1:
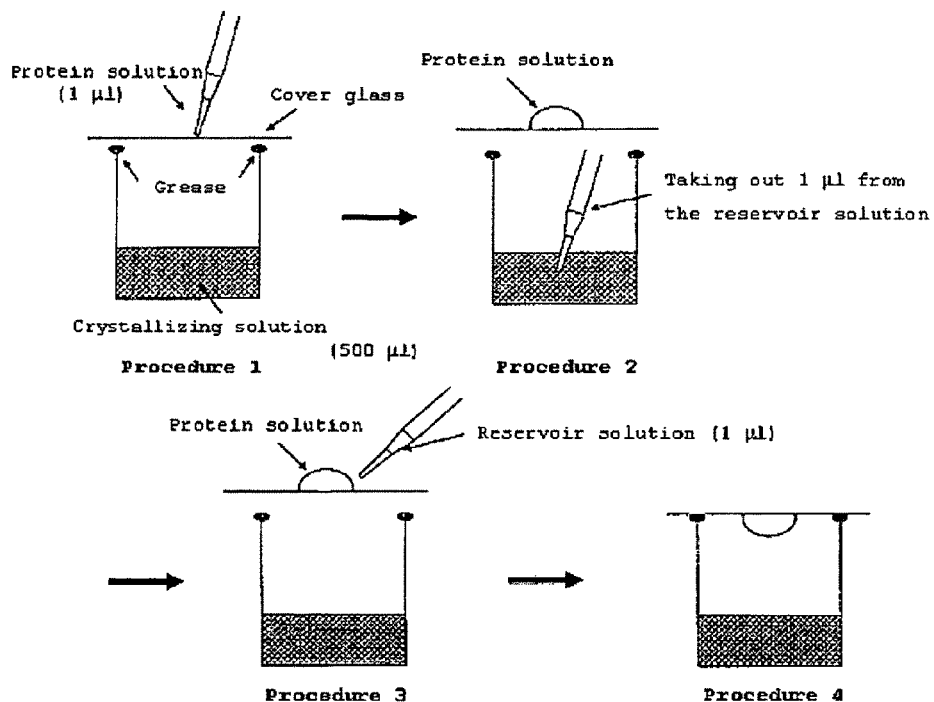
FIG. 1 illustrates an outline of the procedure of the hanging drop diffusion method used for crystallization in Examples 1 to 6.
Figure 2:
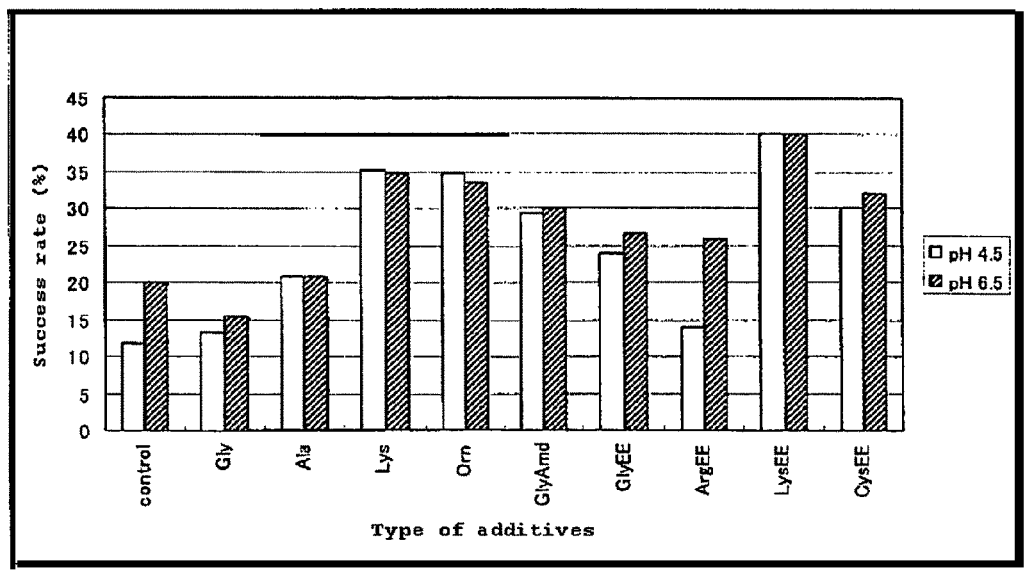
FIG. 2 is a graph showing the results (Tables 2 and 3) of Example 1. More specifically, the figure indicates the crystallization success rate through the use of various amino acids (horizontal axis) in initial screening, with respect to each pH level (pH 4.5 and pH 6.5).
Figure 3:
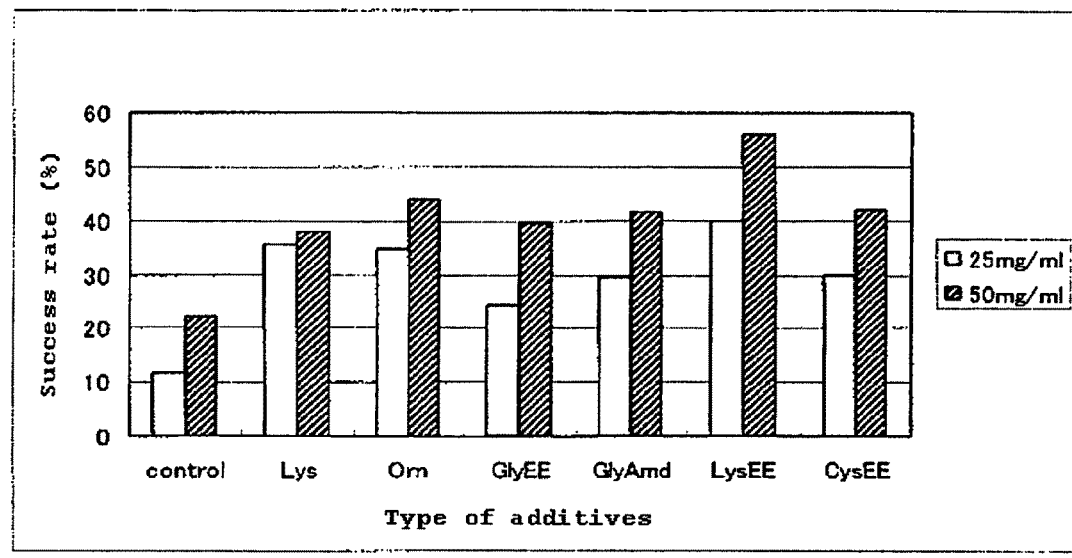
FIG. 3 is a graph showing the results (Tables 4 and 5) of Example 1. More specifically, the figure indicates the crystallization success rate through the use of various amino acids or amino acid derivatives (horizontal axis) in initial screening, with respect to each protein concentration (25 mg/ml and 50 mg/ml) (pH 4.5).
Figure 4:
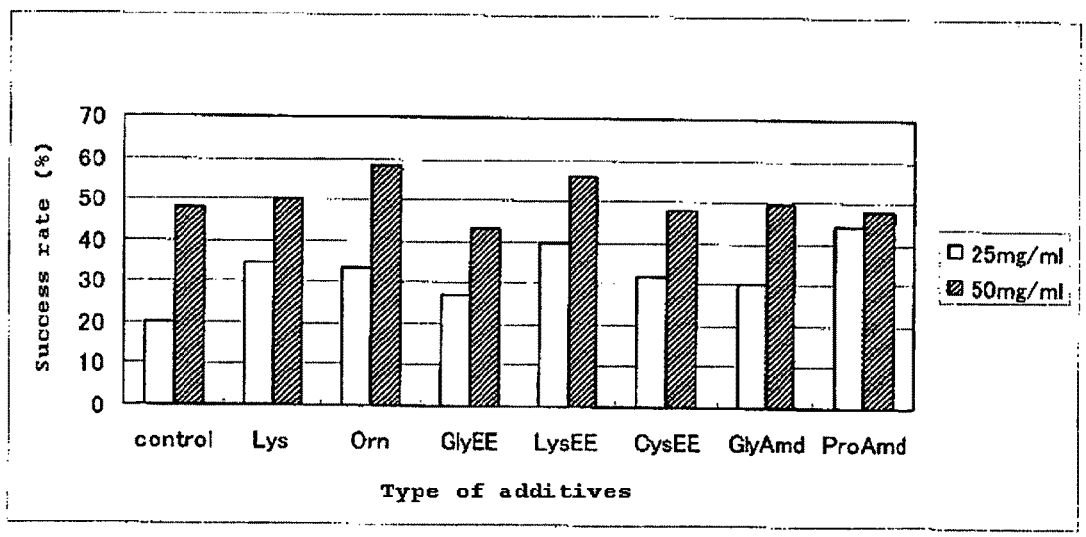
FIG. 4 is a graph showing the results (Table 6) of Example 1. More specifically, the figure shows the crystallization success rate through the use of various amino acids or amino acid derivatives (horizontal axis) in initial screening, with respect to each protein concentration (25 mg/ml and 50 mg/ml) (pH 6.5).
Figure 5:
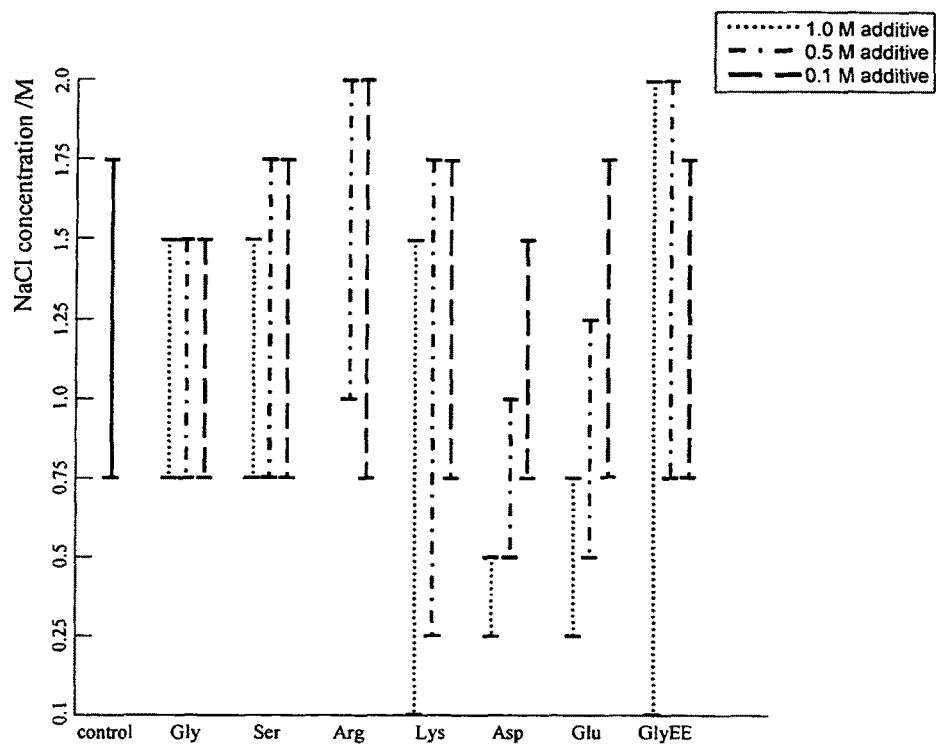
FIG. 5 shows the crystallization state on the 9th day from the beginning of crystallization in Example 2. The vertical axis represents the concentration of the precipitant (NaCl) used for crystallization, and the horizontal axis represents the amino acids and amino acid derivatives used for crystallization. The protein concentration is 25 mg/ml.
Figure 6:
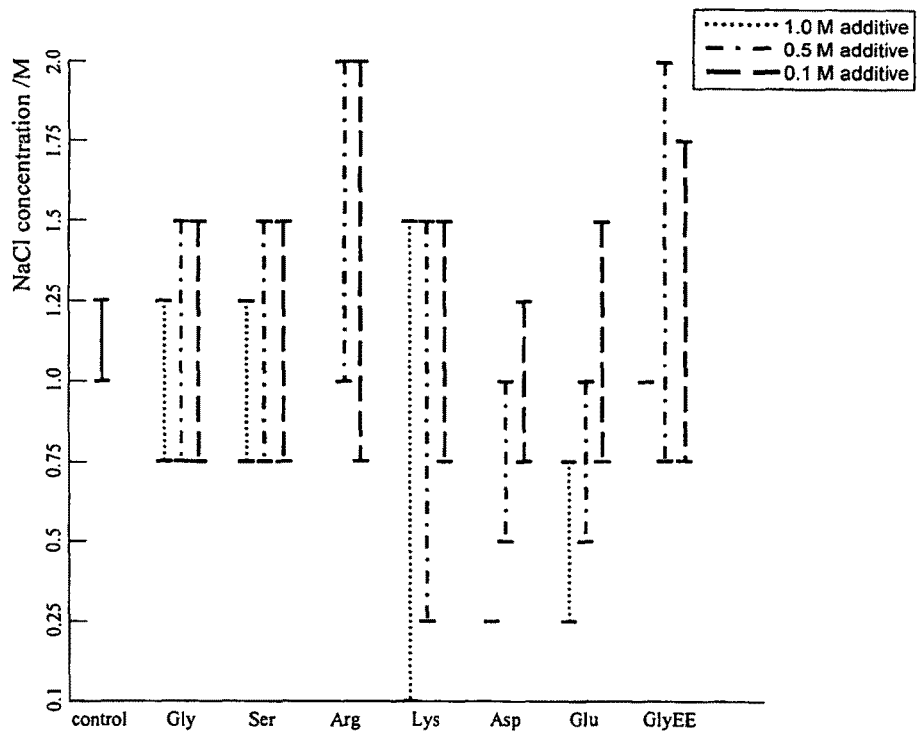
FIG. 6 shows the crystallization state on the 3rd day from the beginning of crystallization in Example 2. The vertical axis represents the concentration of the precipitant (NaCl) used for crystallization, and the horizontal axis represents the amino acids and amino acid derivatives used for crystallization. The protein concentration is 25 mg/ml.
Figure 7:
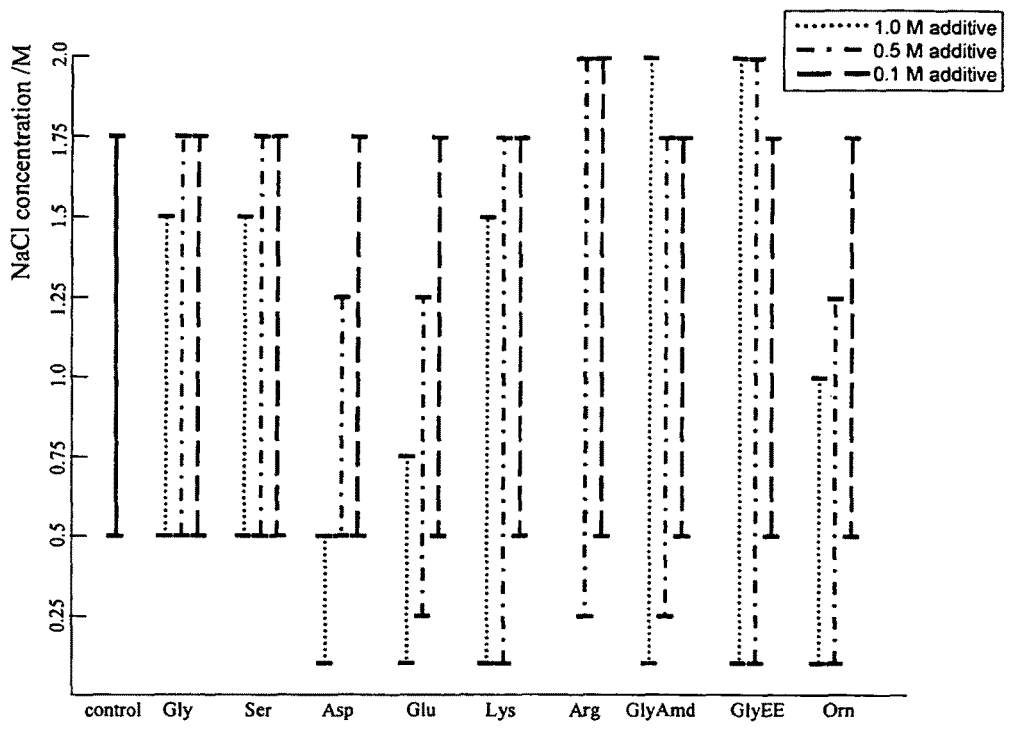
FIG. 7 shows the crystallization state three weeks after the beginning of crystallization in Example 2. The vertical axis represents the concentration of the precipitant (NaCl) used for crystallization, and the horizontal axis represents the amino acids and amino acid derivatives used for crystallization. The protein concentration is 50 mg/ml.
Figure 8:
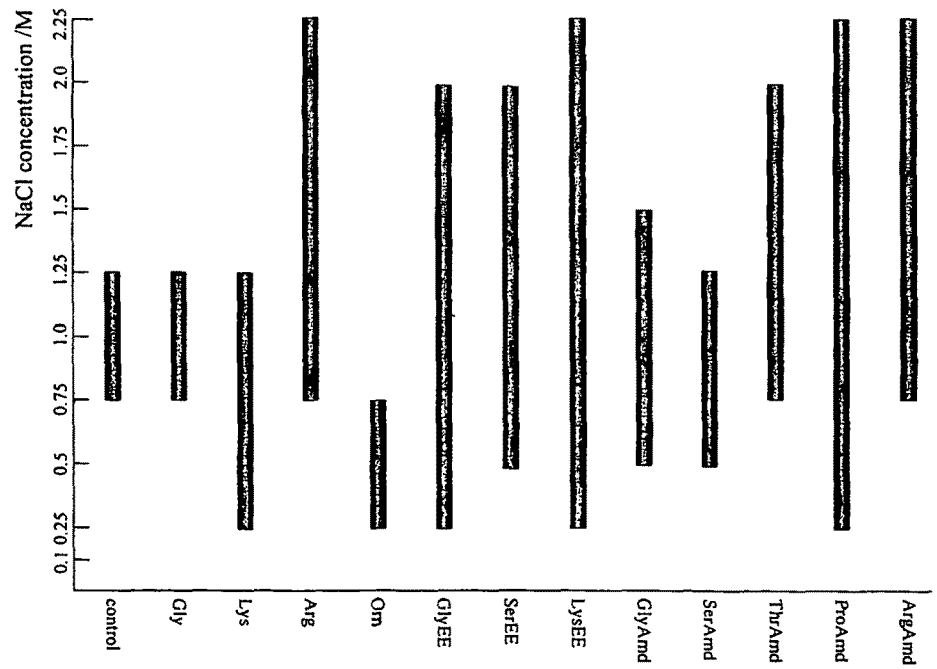
FIG. 8 shows the crystallization state two days after the beginning of crystallization in Experiment 3. The vertical axis represents the concentration of the precipitant (NaCl) used for crystallization, and the horizontal axis represents the amino acids and amino acid derivatives used for crystallization. The protein concentration is 50 mg/ml.
Figure 9:
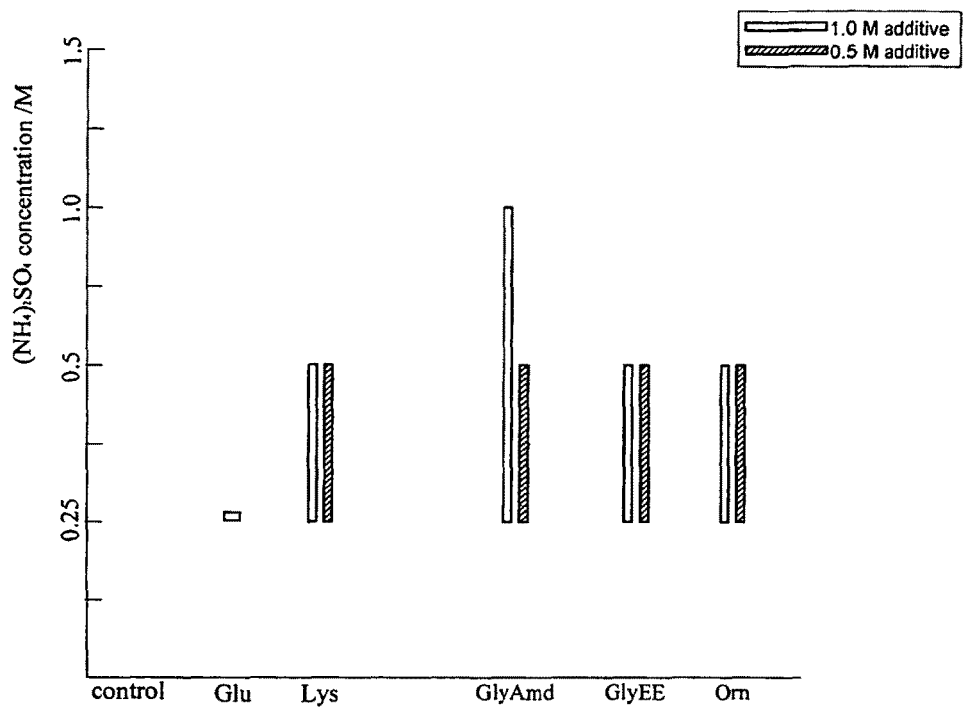
FIG. 9 shows the crystallization state in Example 4. The vertical axis represents the concentration of the precipitant (ammonium sulfate) used for crystallization, and the horizontal axis represents the amino acids and amino acid derivatives used for crystallization. The protein concentration is 100 mg/ml.
Figure 10:
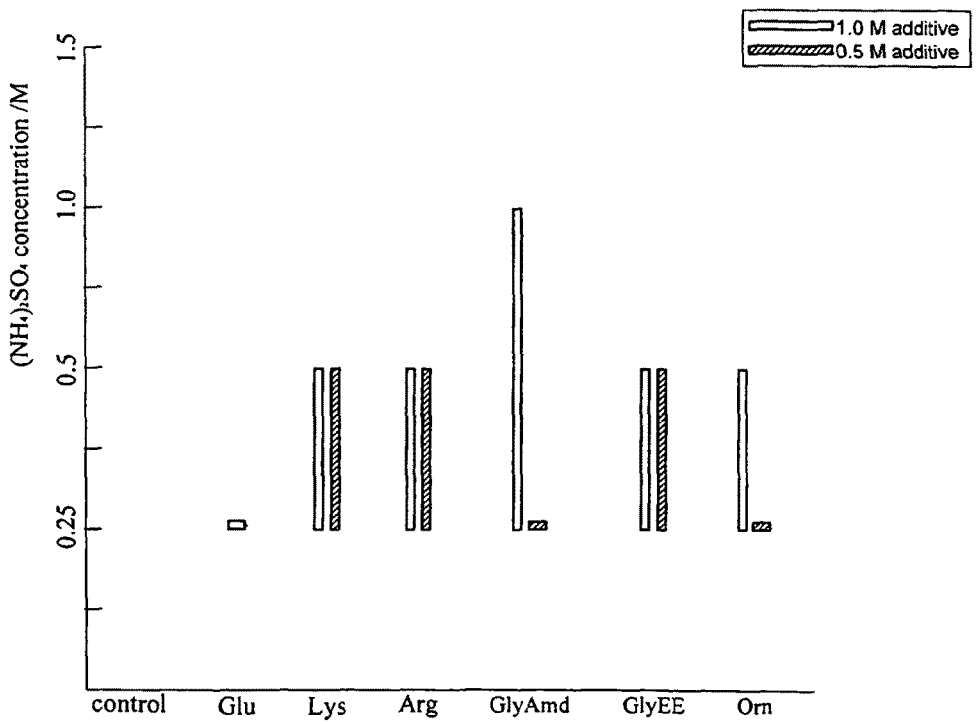
FIG. 10 shows the crystallization state in Example 4. The vertical axis represents the concentration of the precipitant (ammonium sulfate) used for crystallization, and the horizontal axis represents the amino acids and amino acid derivatives used for crystallization. The protein concentration is 150 mg/ml.
Figure 11:
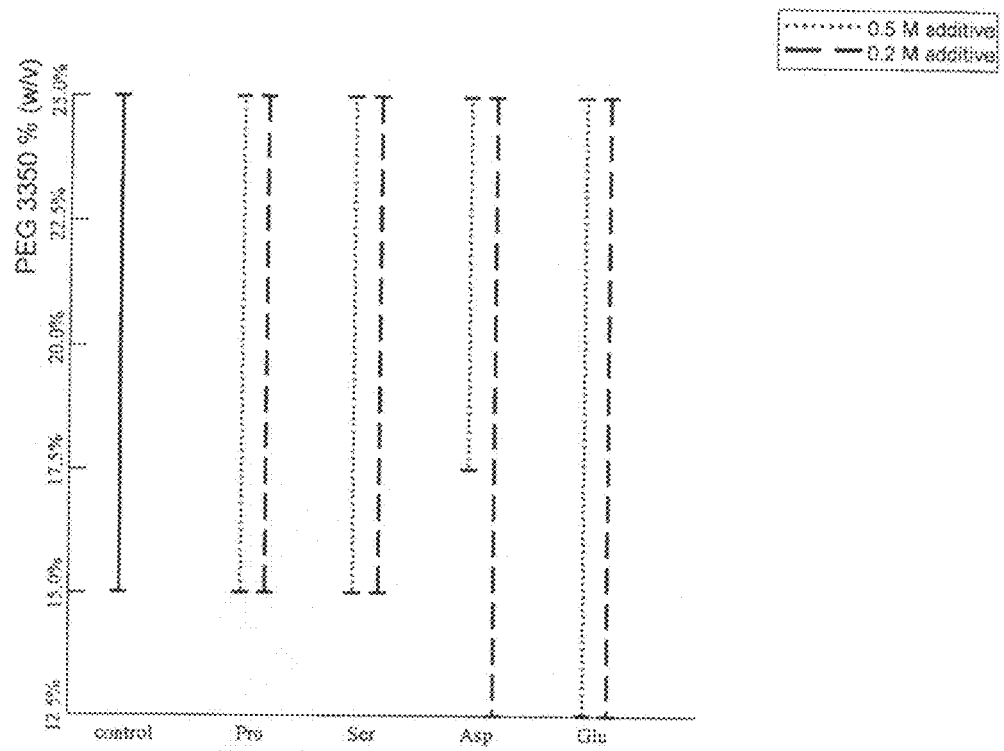
FIG. 11 shows the crystallization state in Example 5. The vertical axis represents the concentration of the precipitant (polyethylene glycol) used for crystallization, and the horizontal axis represents the amino acids and amino acid derivatives used for crystallization.
Figure 12:
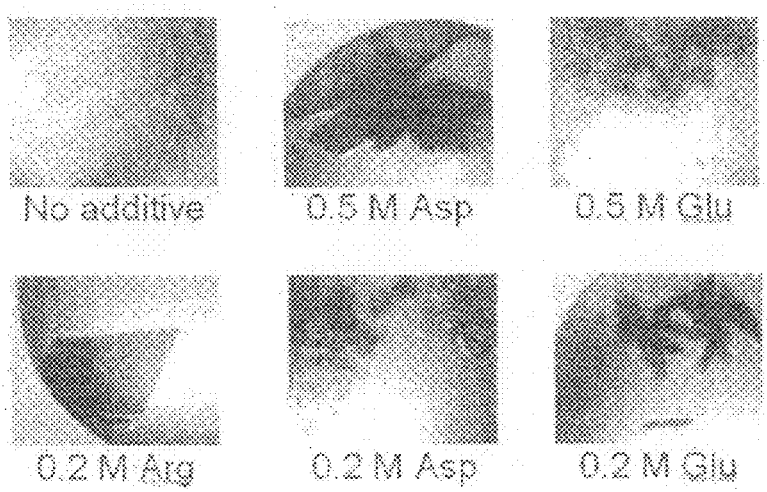
FIG. 12 shows images of the crystals obtained in Example 5, observed under a stereoscopic microscope. In the figure, the image represented by "no additive" shows the protein crystal obtained in the control experiment (control).
Figure 13:
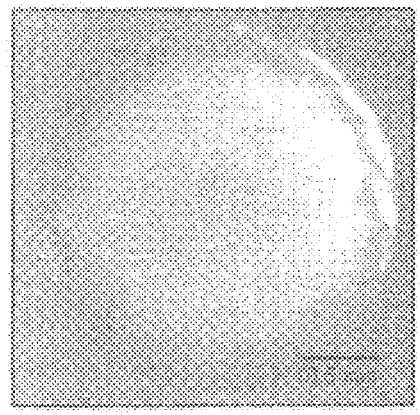
FIG. 13 shows images of the crystals obtained in Example 6, observed under a stereoscopic microscope. In the figure, the image represented by "no additive" shows the appearance of the drop in the control experiment (control). In the control experiment, no crystals but only precipitates were obtained.
Figure 13:
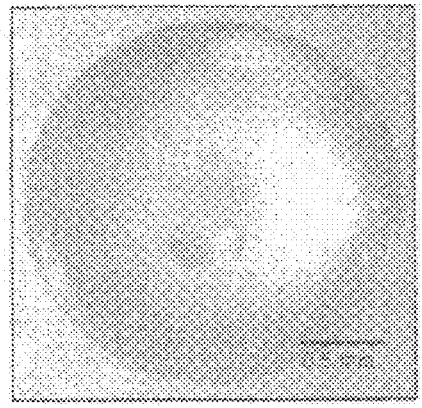
Figure 13:
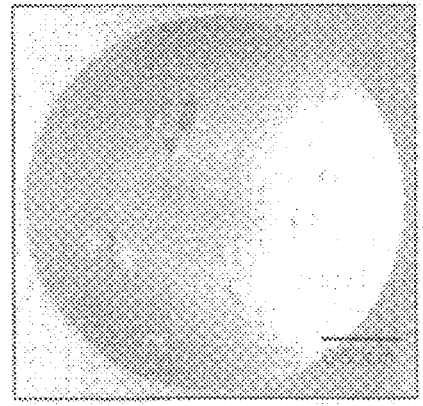
Figure 14:
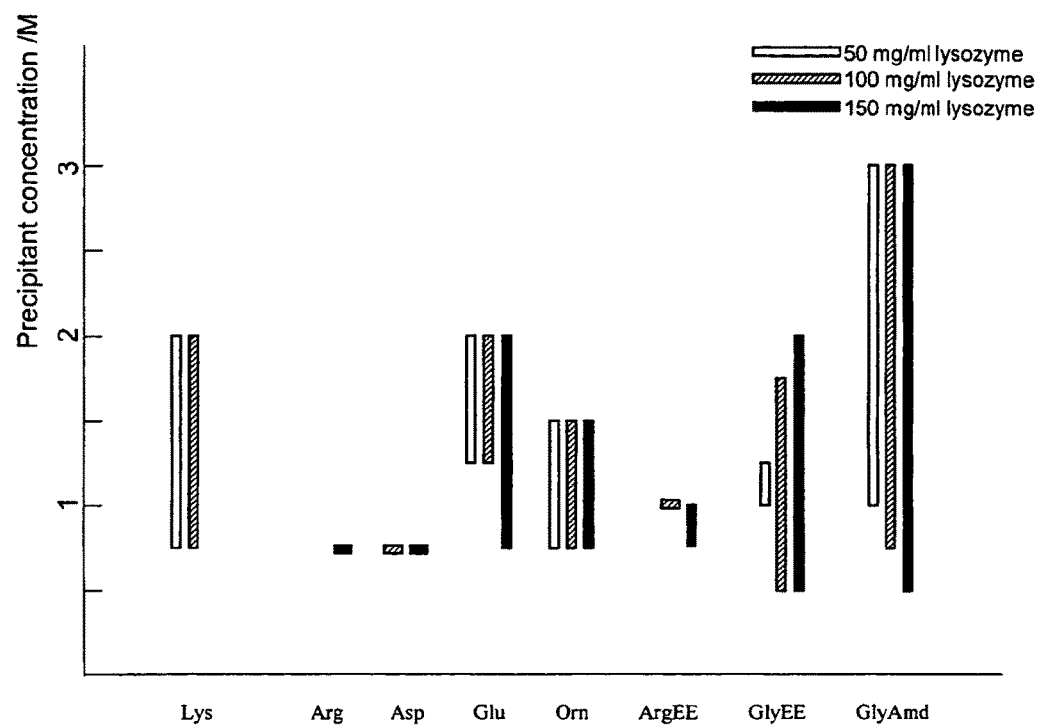
FIG. 14 shows the crystallization state in Example 7. The horizontal axis represents the amino acids, dipeptides, and amino acid derivatives used for crystallization, and the vertical axis represents their concentration.

The invention claimed is:

1. A method for crystallizing a protein, comprising the steps of:
    bringing a protein crystallizing agent into contact with a protein-containing solution, to prepare a mixture; and
    precipitating and crystallizing the protein,
    wherein the protein crystallizing agent comprises at least one compound selected from the group consisting of ornithine, an amide derivative of an amino acid, a salt thereof and a solvate thereof; and
    wherein if the mixture contains ornithine or a salt thereof or a solvate thereof, then the ornithine or the salt thereof or the solvate thereof is contained in the mixture at a concentration of 20 mM or more.

2. The method for crystallizing a protein according to claim 1,
    wherein the protein is precipitated and crystallized in a vapor diffusion method, a batch method, a liquid-liquid diffusion method or a dialysis method.

3. The method for crystallizing a protein according to claim 1,
    wherein the amide derivative of an amino acid is glycinamide, serinamide, threonine amide, argininamide, or prolinamide.

4. A method for screening for protein crystallization conditions, comprising the steps of:
    bringing a protein crystallizing agent into contact with a protein-containing solution, to prepare a mixture; and
    observing the occurrence of precipitation of the protein to screen for protein crystallization conditions,
    wherein the protein crystallizing agent comprises at least one compound selected from the group consisting of ornithine, an amide derivative of an amino acid, a salt thereof and a solvate thereof; and
    wherein if the mixture contains ornithine or a salt thereof or a solvate thereof, then the ornithine or the salt thereof or the solvate thereof is contained in the mixture at a concentration of 20 mM or more.

5. The method for screening for protein crystallization conditions according to claim 4,
    wherein the protein is precipitated and crystallized in a vapor diffusion method.

6. The method for screening for protein crystallization conditions according to claim 4,
    wherein the amide derivative of an amino acid is glycinamide, serinamide, threonine amide, argininamide, or prolinamide.

7. A method for crystallizing a protein, comprising the steps of:
    bringing a protein crystallizing agent into contact with a protein-containing solution, to prepare a mixture; and
    precipitating and crystallizing the protein,
    wherein the protein crystallizing agent comprises at least one compound selected from the group consisting of an amide derivative of an amino acid, a salt thereof and a solvate thereof.

8. The method for crystallizing a protein according to claim 7,
    wherein the amide derivative of an amino acid is glycinamide, serinamide, threonine amide, argininamide, or prolinamide.

9. A method for screening for protein crystallization conditions, comprising the steps of:
    bringing a protein crystallizing agent into contact with a protein-containing to prepare a mixture; and
    observing the occurrence of precipitation of the protein to screen for protein crystallization conditions,
    wherein the protein crystallizing agent comprises at least one compound selected from the group consisting of an amide derivative of an amino acid, a salt thereof and a solvate thereof.

10. The method for screening for protein crystallization conditions according to claim 9,
    wherein the amide derivative of an amino acid is glycinamide, serinamide, threonine amide, argininamide, or prolinamide.

* * * * *